US006660738B2

(12) United States Patent
Aebi et al.

(10) Patent No.: US 6,660,738 B2
(45) Date of Patent: Dec. 9, 2003

(54) PYRROLIDINE DERIVATIVES

(75) Inventors: Johannes Aebi, Basel (CH); Daniel Bur, Therwil (CH); Alexander Chucholowski, San Diego, CA (US); Henrietta Dehmlow, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/906,983

(22) Filed: Jul. 17, 2001

(65) Prior Publication Data

US 2002/0055632 A1 May 9, 2002

(30) Foreign Application Priority Data

Jul. 19, 2000 (EP) .............................. 00114950

(51) Int. Cl.⁷ .................... C07D 401/04; C07D 403/04; A61K 31/4439; A61K 31/506
(52) U.S. Cl. ............................ 514/252.05; 514/252.02; 514/252.11; 514/255.05; 514/275; 514/343; 544/229; 544/238; 544/295; 544/296; 544/327; 544/331; 544/332; 544/336; 544/357; 546/256; 546/278.4
(58) Field of Search ................................ 544/229, 238, 544/327, 331, 332, 336, 295, 296, 357; 514/252.05, 255.05, 275, 343, 252.02, 252.11; 546/278.4, 256

(56) References Cited

U.S. PATENT DOCUMENTS 4,962,103 A  10/1990  Sunagawa et al. .......... 514/210

FOREIGN PATENT DOCUMENTS

| EP | 0 411 664 | 2/1991 |
| EP | 0 521 524 | 1/1993 |
| EP | 0 528 678 | 2/1993 |
| EP | 0 848 004 | 6/1998 |
| WO | WO 97/41120 | 11/1997 |
| WO | WO 98/08814 | 3/1998 |
| WO | WO 99/14195 | 3/1999 |
| WO | WO 99/52868 | 10/1999 |

OTHER PUBLICATIONS

Bertenshaw et al., PubMed Abstract (J. Biol. Chem. 278(4):2522–32), Jan. 2003.*
Yanagisawa, M. et al. Nature (Mar. 31, 1998), 332 (6/63), pp. 411–415.
Xu, D., et al., Cell (1994) vol. 78 pp. 473–485.
Oefner, et al., J. Mol. Biol. (2000) 296, pp. 341–349.

* cited by examiner

Primary Examiner—Deepak Rao
(74) Attorney, Agent, or Firm—George W. Johnston; John P. Parise

(57) ABSTRACT

The present invention relates to pyrrolidine derivatives useful as inhibitors of metalloproteases, e.g. zinc proteases, and which are effective in treating disease states associated with vasoconstriction.

28 Claims, No Drawings

PYRROLIDINE DERIVATIVES

BACKGROUND OF THE INVENTION

Endothelins are peptides, that exist in three isoforms ET-1, ET-2, and ET-3, each encoded by a distinct gene. They have been originally discovered in the conditioned medium of porcine endothelial cells in 1988 by Yanagisawa (Yanagisawa M; Kurihara H; Kimura S; Tomobe Y; Kobayashi M; Mitsui Y; Yazaki Y; Goto K; Masaki T: A novel potent vasoconstrictor peptide produced by vascular endothelial cells [see comments]. NATURE (Mar. 31, 1988), 332(6163), 411-5.). The active ETs are peptides of 21 amino acids with two intramolecular disulfide bridges. They are produced from preproproteins of 203 to 212 amino acids which are processed by furin-like endopeptidases to the biologically inactive big-endothelin (big-ET). The big-ETs are specifically processed to mature ETs by a hydrolytic cleavage between amino acids 21 and 22 that are $Trp^{21}$-$Val^{22}$ (big-ET-1, big ET-2) and $Trp^{21}$-$Ile^{22}$ in big-ET-3 respectively. Already in 1988 a specific metalloprotease was postulated to be responsible for this specific cleavage. In 1994, ECE-1 (endothelin converting enzyme-1) was purified and cloned from bovine adrenal (Xu D, Emoto N, Giaid A, Slaughter C, Kaw S, de Witt D, Yanagisawa M: ECE-1: a membrane-bound metalloprotease that catalyzes the proteolytic activation of big endothelin-1. Cell (1994) 78: 473–485).

ECE-1 is a membrane bound type II zinc-endopeptidase with a neutral pH optimum and a zinc binding motif HExxHx(>20)E. It belongs to subfamily M13 and has a large 681 amino acid ectodomain that comprises the active site. Other members of the M13 family are NEP24.11 (neutral endopeptidase), PEX, a phosphate regulating neutral endopeptidase, and Kell blood group protein that has recently been described as a big-ET-3 processing enzyme. Members of the M13 family of human origin are characterized by a high molecular weight (>80 kDa) a number of conserved disulfide bridges and a complex glycosylation pattern. The structure of NEP has recently been solved. (Oefner et al, J. Mol. Biol. 2000, 296, 341–349). The catalytic domain of ECE and related human M13 proteinases are significantly larger (>650 amino acids) than members of matrix metalloproteases (MMPs). Unlike the family of the MMPs which belong to the metzincins and display a typical HExxHxxGxxH pattern members of the M13 family are gluzincins comprising a HExxHx(>20)E pattern. These two families are clearly different in size of catalytic domains, structure and zinc coordinating pattern of ligands. Active sites of the two families show clear differences which has clear impact on type of inhibitors and the potential selectivity.

SUMMARY OF THE INVENTION

The present invention relates to compounds of formula (I)

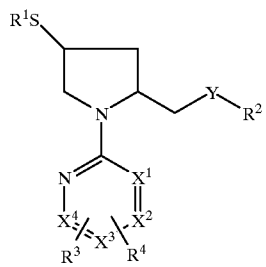

wherein
$R^1$ is hydrogen, alkylcarbonyl or arylcarbonyl;
$R^2$ is alkyl, alkinyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl(alkoxycarbonyl)alkyl, arylaminocarbonyl, diarylalkyl, aryl(carboxyalkyl)aminocarbonyl, arylcarbonyl, arylsulfonyl, cycloalkyl, cycloalkylcarbonyl, cycloalkylalkyl, heteroaryl, heteroarylalkyl, heterocyclylalkyl or the group $YR^2$ is heterocyclyl;
$R^3$ and $R^4$ are independently selected from the group consisting of hydrogen, alkyl, alkylcycloalkyl, alkylcycloalkylalkyl, alkylthio, cycloalkyl, cycloalkylalkyl, carbamoyl, carboxy, carboxyalkyl, cyano, amino, mono- and dialkylamino, alkoxy, alkoxyalkyl, alkoxycarbonyl, alkoxycarbonylalkyl, alkenyl, alkinyl, aryl, arylalkyl, arylalkyl (alkoxycarbonyl)alkyl, arylcarbonylalkyl, arylalkenyl, aryl(alkoxycarbonyl)alkyl, arylamino, arylalkylamino, aryloxy, halogen, heteroaryl, heteroarylalkyl, heterocyclyl, heterocyclylalkyl, trimethylsilanylethynyl or trifluormethyl;
$R^5$ is hydrogen, alkyl, aryl, arylalkyloxycarbonyl, or alkylcarbonyl;
$X^1$, $X^2$, $X^3$ and $X^4$ are CH or N with the proviso that only up to two groups of $X^1$, $X^2$, $X^3$ and $X^4$ are N;
Y is —O— or —$NR^5$—; and
dimeric forms, and/or pharmaceutically acceptable esters, and/or pharmaceutically acceptable salts thereof, preferably pharmaceutically acceptable esters, and/or pharmaceutically acceptable salts thereof, and most preferably pharmaceutically acceptable salts thereof.

The present invention is directed to compounds which are useful as inhibitors of metalloproteases, e.g. zinc proteases, particularly zinc hydrolases, and which are effective in the prophylaxis and treatment of disease states which are associated with vasoconstriction of increasing occurrences. Examples of such disorders are high blood pressure, coronary disorders, cardiac insufficiency, renal and myocardial ischaemia, renal insufficiency, dialysis, cerebral ischaemia, cardiac infarct, migraine, subarachnoid haemorrhage, Raynaud syndrome and pulmonary high pressure. In addition the compounds are useful as cytostatic and cerebroprotective agents for inhibition of graft rejection, for organ protection and for treatment of ophthalmological diseases.

DETAILED DESCRIPTION OF THE INVENTION

The present invention is directed to compounds of formula (I):

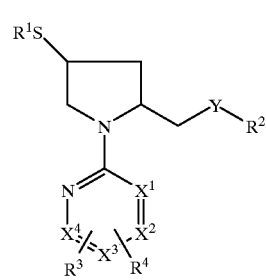

wherein
$R^1$ is hydrogen, alkylcarbonyl or arylcarbonyl;
$R^2$ is alkyl, alkinyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl(alkoxycarbonyl)alkyl, arylaminocarbonyl, diarylalkyl, aryl(carboxyalkyl) aminocarbonyl, arylcarbonyl, arylsulfonyl, cycloalkyl, cycloalkylcarbonyl, cycloalkylalkyl, heteroaryl, heteroarylalkyl, heterocyclylalkyl or the group $YR^2$ is heterocyclyl;

$R^3$ and $R^4$ are independently selected from the group consisting of hydrogen, alkyl, alkylcycloalkyl, alkylcycloalkylalkyl, alkylthio, cycloalkyl, cycloalkylalkyl, carbamoyl, carboxy, carboxyalkyl, cyano, amino, mono- and dialkylamino, alkoxy, alkoxyalkyl, alkoxycarbonyl, alkoxycarbonylalkyl, alkenyl, alkinyl, aryl, arylalkyl, arylalkyl (alkoxycarbonyl)alkyl, arylcarbonylalkyl, arylalkenyl, aryl(alkoxycarbonyl)alkyl, arylamino, arylalkylamino, aryloxy, halogen, heteroaryl, heteroarylalkyl, heterocyclyl, heterocyclylalkyl, trimethylsilanylethynyl or trifluormethyl;

$R^5$ is hydrogen, alkyl, aryl, arylalkyloxycarbonyl, or alkylcarbonyl;

$X^1$, $X^2$, $X^3$ and $X^4$ are CH or N with the proviso that only up to two groups of $X^1$, $X^2$, $x^3$ and $X^4$ are N;

Y is —O— or —$NR^5$—; and dimeric forms, and/or pharmaceutically acceptable esters, and/or pharmaceutically acceptable salts thereof.

The term "alkyl", alone or in combination, means a straight-chain or branched-chain alkyl group containing a maximum of 7, preferably a maximum of 4, carbon atoms, e.g., methyl, ethyl, n-propyl, 2-methylpropyl (iso-butyl), 1-methylethyl (iso-propyl), n-butyl, and 1,1-dimethylethyl (t-butyl).

The term "carboxy" refers to the group —C(O)OH.

The term "carbamoyl" refers to the group —C(O)$NH_2$.

The term "carbonyl" refers to the group —C(O)—.

The term "halogen" refers to the group fluoro, bromo, chloro and iodo.

The term "sulfonyl" refers to the group —S($O_2$)—.

The term "alkenyl" refers to a hydrocarbon chain as defined for alkyl having at least one olefinic double bond (including for example, vinyl, allyl and butenyl).

The term "alkinyl" refers to a hydrocarbon chain as defined for alkyl having at least one olefinic triple bond (including for example propinyl, butin-(1)-yl, etc.).

The term "alkoxy", alone or in combination, means an alkyl ether group in which the term 'alkyl' has the significance given earlier, such as methoxy, ethoxy, n-propoxy, isopropoxy, n-butoxy, isobutoxy, sec.butoxy, tert.butoxy and the like.

The term "alkoxycarbonyl" refers to a group of the formula —C(O)$R_c$ wherein $R_c$ is alkoxy as defined above.

The term "hydroxy" refers to the group —OH, the term "cyano" to the group —CN.

The term "hydroxyalkyl" means an alkyl group as defined above which is substituted by a hydroxy group.

The term "thioalkyl" and "cyanoalkyl" refer to an alkyl group as defined above which is substituted by a —SH group or an —CN group, respectively.

"Carboxyalkyl" means a lower-alkyl as defined above which is substituted by a HOOC— group.

The term "alkylcarbonyl", alone or in combination, means an acyl group derived from an alkanecarboxylic acid, i.e. alkyl—C(O)—, such as acetyl, propionyl, butyryl, valeryl, 4-methylvaleryl etc.

The term "cycloalkyl" signifies a saturated, cyclic hydrocarbon group with 3–8, preferably 3–6 carbon atoms, i.e. cyclopropyl, cyclobutyl, cyclopentyl and cyclohexyl and the like.

The term "amino" refers to the group —$NH_2$.

The term "aryl" for $R^2$— alone or in combination—, refers to an aromatic carbocyclic radical, i.e. a 6 or 10 membered aromatic or partially aromatic ring, e.g. phenyl, naphthyl or tetrahydronaphthyl, preferably phenyl or naphthyl, and most preferably phenyl. The aryl moiety is optionally substituted with one or more groups independently selected from halogen, preferably fluor, alkoxycarbonyl, e.g. methylcarbonyl, carboxy, cyano, alkyl, alkoxy, phenyl, phenoxy, trifluormethyl, trifluormethoxy, 1,3-dioxolyl, or 1,4-dioxolyl, more preferably fluor, alkoxycarbonyl, alkyl, trifluoromethyl and trifluoromethoxy and most preferably fluor. The most preferred aromatic groups are 2,5-difluorobenzyl and 2,4,5-trifluorobenzyl.

The term "aryl" for $R^3$ and $R^4$—alone or in combination—, refers to an aromatic carbocyclic radical, i.e. a 6 or 10 membered aromatic or partially aromatic ring, e.g. phenyl, naphthyl or tetrahydronaphthyl, preferably phenyl or naphthyl, and most preferably phenyl. The aryl moiety is optionally substituted with one or more groups independently selected from halogen, alkoxycarbonyl, e.g. methylcarbonyl, carboxy, cyano, alkyl, alkoxy, phenyl, phenoxy, trifluormethyl, trifluormethoxy, 1,3-dioxolyl, or 1,4-dioxolyl, cyclohexyl, hydroxy, alkylamido, e.g. acetamido, nitro, alkylsulfonyl, e.g. methylsulfonyl, more preferably fluor, chlor, brom, alkoxy, carboxy, 1,4-dioxolyl, alkoxycarbonyl. The most preferred aromatic groups for $R^3$ and $R^4$ are phenyl and phenoxy.

The term "aryl" for $R^5$ refers to phenyl optionally substituted with alkyl, alkoxy or halogen.

The term "aryloxy" refers to an aryl group as defined above attached to a parent structure via an oxy radical, i.e., aryl-O—.

The term "heteroaryl" for $R^2$—alone or in combination— refers to an aromatic mono- or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are thiophenyl, isoxazolyl, thiazolyl, pyridinyl, pyrrolyl, imidazolyl, tetrazolyl, preferably pyridinyl, isoxazolyl and thiazolyl. Optionally, the heteroaryl group can be mono-, di- or tri-substituted, independently, with phenyl, alkyl, alkylcarbonyl, alkoxycarbonyl, hydroxy, amino, alkylamino, dialkylamino, carboxy, alkoxycarbonylalkyl, preferably alkyl.

The term "heteroaryl" for $R^3$ and $R^4$—alone or in combination—refers to an aromatic mono- or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are pyridinyl, thiophenyl, isoxyzolyl, isoquinolyl, quinolyl, and 1H-benzo[d][1,3]oxazin-2,4-dione and indolyl, pyrimidine, pyridazine, and pyrazine, preferably pyridinyl and thiophenyl. Optionally, the heteroaryl group can be mono, di- or tri-substituted, independently, with alkyl, alkoxy, halogen, alkylcarbonyl, alkoxycarbonyl, hydroxy, amino, alkylamino, dialkylamino, carboxy, alkoxycarbonylalkyl, preferably alkyl.

The term "heterocyclyl" —alone or in combination— refers to a non-aromatic mono- or bicyclic radical having 5 to 10, preferably 5 to 6 ring atoms, containing one to three heteroatoms, preferably one heteroatom, e.g. independently selected from nitrogen, oxygen or sulfur. Optionally the heterocyclic ring can be substituted by a group independently selected from halogen, alkyl, alkoxy, oxocarboxy, alkoxycarbonyl, etc. and/or on a secondary nitrogen atom (i.e. —NH—) by alkyl, arylalkoxycarbonyl, alkylcarbonyl or on a tertiary nitrogen atom (i.e. =N—) by oxido.

Examples for heterocyclic groups are morpholinyl, pyrrolidinyl, piperidyl, etc.

The term "dimeric form" means a compound wherein the two $R^1$ groups of two identical compounds of formula I have been replaced by a common single bond or wherein $R^1$ is glutathione-S— or cysteine-S— or ester and/or alkylcarbonyl or arylcarbonyl derivatives thereof, e.g. acetylcysteine-S— or benzoylcysteine-S—, preferably glutathione-S—, cysteine-S—, acetylcysteine-S— or benzoylcysteine-S—.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) are useful in inhibiting mammalian metalloprotease activity, particularly zinc hydrolase activity. More specifically, the compounds of formula (I) are useful as medicaments for the treatment and prophylaxis of disorders which are associated with diseases caused by endothelin-converting enzyme (ECE) activity. Inhibiting of this enzyme would be useful for treating myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma. In addition the compounds are useful as cytostatic and cerebroprotective agents, for inhibition of graft rejection, for organ protection and for treatment of ophthalmological diseases.

A preferred embodiment of the present invention encompasses compounds of general formula (II)

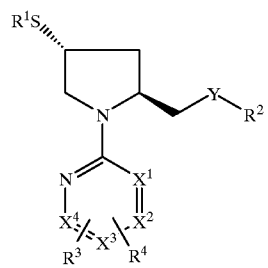

(II)

wherein $R^1$, $R^2$, $R^3$, $R^4$, $X^1$, $X^2$, $X^3$, $X^4$ and Y are as defined in formula 1.

In a preferred embodiment of the invention $R^1$ is selected from hydrogen or alkylcarbonyl, more preferably from hydrogen or acetyl and most preferably $R^1$ is hydrogen.

In the above compounds $R^2$ is preferably alkyl, alkinyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl (alkoxycarbonyl)alkyl, arylcarbamoyl, diarylalkyl, aryl (carboxyalkyl)amide, arylcarbonyl, arylsulfonyl, cycloalkyl, cycloalkylcarbonyl, cycloalkylalkyl, heteroaryl, heteroarylalkyl or heterocyclylalkyl, more preferably $R^2$ is aryl, arylalkyl, arylalkoxyalkyl, arylaminocarbonyl, arylcarbonyl, arylsulfonyl, cycloalkyl, cycloalkylcarbonyl, cycloalkylalkyl or heteroarylalkyl, even more preferably $R^2$ is aryl, arylalkyl, arylcarbamoyl, arylamino, arylcarbonyl, arylsulfonyl or heteroarylalkyl and most preferably $R^2$ is arylalkyl. In an especially preferred embodiment of the present invention $R^2$ is phenylalkyl optionally substituted with 2 to 3 halogen atoms, preferably fluor atoms.

In the compounds of the present invention, preferably $R^3$ and $R^4$ are independently selected from the group consisting of hydrogen, alkyl, alkylthio, alkenyl, alkoxy, alkoxycarbonyl, amino, aryl, arylalkyl, arylalkenyl, arylalkylamino, aryloxy, mono- and dialkylamino, carbamoyl, carboxy, cyano, halogen, heteroaryl, heteroarylalkyl, trimethylsilanylethynyl and trifluoromethyl, more preferably $R^3$ and $R^4$ are independently selected from the group consisting of hydrogen, alkyl, alkoxy, alkoxycarbonyl, alkenyl, thiophenyl, amino, mono- and dialkylamino, carboxy, cyano, halogen, trimethylsilanylethynyl, phenylalkylamino, pyridinyl, pyrimidinyl, pyrazinyl, phenyl, and phenoxy, wherein the aryl and heteroaryl groups are optionally substituted with alkyl, alkoxy, carboxy, or halogen. In the most preferred embodiment of the present invention $R^3$ is hydrogen, alkyl, alkoxy, alkoxycarbonyl, alkenyl, thiophenyl, amino, mono- and dialkylamino, carboxy, cyano, halogen, trimethylsilanylethynyl, phenylalkylamino, pyridinyl, pyrimidinyl, pyrazinyl, phenyl, and phenoxy, wherein the aryl and heteroaryl groups are optionally substituted with alkyl, alkoxy, carboxy, or halogen, and $R^4$ is hydrogen.

In a further preferred embodiment of the present invention Y is —$NR^5$—$R^5$ being hydrogen or alkyl and more preferably hydrogen.

In another preferred embodiment of the present invention Y is —O—.

The invention also relates to the above defined compounds wherein $X^1$ is N and $X^2$, $X^3$ and $X^4$ are CH, or wherein $X^2$ is N and $X^1$, $X^3$ and $X^4$ are CH or wherein $X^3$ is N and $X^1$, $X^2$ and $X^4$ are CH or wherein $X^1$, $X^2$, $X^3$ and $X^4$ are CH.

A preferred embodiment the present invention comprises compounds as defined above wherein $R^1$ is hydrogen or alkylcarbonyl, $R^2$ is phenylalkyl substituted with 2 to 3 halogen; $R^3$ is selected from hydrogen, alkyl, alkoxy, alkoxycarbonyl, alkenyl, thiophenyl, amino, mono- and dialkylamino, carboxy, cyano, halogen, trimethylsilanylethynyl, phenylalkylamino, pyridinyl, pyrimidinyl, pyrazinyl, phenyl, or phenoxy, and wherein the aryl and heteroaryl groups are optionally substituted with alkyl, alkoxy, carboxy, or halogen; $R^4$ is hydrogen; $X^1$, $X^2$, $X^3$ and $X^4$ are CH or N with the proviso that only up to two groups of $X^1$, $X^2$, $X^3$ and $X^4$ are N; and Y is —NH— or —O—. In a preferred embodiment $R^1$ is hydrogen or acetyl and $R^2$ is difluorobenzyl or trifluorobenzyl in the above defined compounds.

Preferred embodiments of the present invention are the compounds exemplified in the examples. Especially the present invention comprises compounds selected from the group consisting of a) (3R,5S)-1-Pyrimidin-2-yl-5-(2,4,5-trifluoro-benzyloxymethyl)-pyrrolidine-3-thiol trifluoro-acetate (1:1);
b) (3R,5S)-1-(4,6-Dimethoxy-pyrimidin-2-yl)-5-(2,4,5-trifluoro-benzyloxymethyl)-pyrrolidine-3-thiol;
c) (3R,5S)-1-(4-Amino-5-fluoro-pyrimidin-2-yl)-5-(2,4,5-trifluoro-benzyloxymethyl)-pyrrolidine-3-thiol;
d) 2-[(2S,4R)-4-Mercapto-2-(2,4,5-trifluoro-benzyloxymethyl)-pyrrolidin-1-yl]-nicotinonitrile;
e) (3R,5S)-1-(6-Phenyl-pyridazin-3-yl)-5-(2,4,5-trifluoro-benzyloxymethyl)-pyrrolidine-3-thiol;
f) 2-[(2S,4R)-4-Mercapto-2-(2,4,5-trifluoro-benzyloxymethyl)-pyrrolidin-1-yl]-nicotinic acid;
g) 2-[(2S,4R)-4-Mercapto-2-(2,4,5-trifluoro-benzyloxymethyl)-pyrrolidin-1-yl]-6-methyl-pyrimidine-4-carboxylic acid methyl ester;
h) 2-[(2S,4R)-4-Mercapto-2-(2,4,5-trifluoro-benzyloxymethyl)-pyrrolidin-1-yl]-4-trifluoromethyl-pyrimidine-5-carboxylic acid methyl ester;
i) (3R,5S)-1-Pyrazin-2-yl-5-(2,4,5-trifluoro-benzyloxymethyl)-pyrrolidine-3-thiol; compound with trifluoro-acetic acid;
j) 2-[(2S,4R)-4-Mercapto-2-(2,4,5-trifluoro-benzyloxymethyl)-pyrrolidin-1-yl]-nicotinamide;
k) (3R,5S)-5-(2,5-Difluoro-4-methoxy-benzyloxymethyl)-1-(2-methoxy-pyrimidin-4-yl)-pyrrolidine-3-thiol;
l) (3R,5S)-1-(2-Chloro-pyrimidin-4-yl)-5-(2,4,5-trifluoro-benzyloxymethyl)-pyrrolidine-3-thiol; compound with trifluoro-acetic acid;
m) (3R,5S)-1-(5-Ethyl-pyrimidin-2-yl)-5-(2,4,5-trifluoro-benzyloxymethyl)-pyrrolidine-3-thiol trifluoro-acetate (1:1);
n) (3R,5S)-1-(5-Propyl-pyrimidin-2-yl)-5-(2,4,5-trifluoro-benzyloxymethyl)-pyrrolidine-3-thiol trifluoro-acetate (1:1);
o) (3R,5S)-5-(2,4,5-Trifluoro-benzyloxymethyl)-1-(4-trifluoromethyl-pyrimidin-2-yl)-pyrrolidine-3-thiol trifluoro-acetate (1:1);
p) (3R,5S)-5-(2,4,5-Trifluoro-benzyloxymethyl)-1-(5-trifluoromethyl-pyridin-2-yl)-pyrrolidine-3-thiol trifluoro-acetate (1:1);
q) (3R,5S)-1-Pyridin-2-yl-5-(2,4,5-trifluoro-benzyloxymethyl)-pyrrolidine-3-thiol trifluoro-acetate (1:1);
r) (2S,4R)-2-[4-Mercapto-2-(2,4,5-trifluoro-benzyloxymethyl)-pyrrolidin-1-yl]-6-methyl-pyrimidine-4-carboxylic acid;
s) (3R,5S)-1-(2-Methoxy-pyrimidin-4-yl)-5-(2,4,5-trifluoro-benzyloxymethyl)-pyrrolidine-3-thiol;
t) (3R,5S)-1-(2-Phenylamino-pyrimidin-4-yl)-5-(2,4,5-trifluoro-benzyloxymethyl)-pyrrolidine-3-thiol trifluoro-acetate (1:1);
u) (3R,5S)-1-(2-Benzylamino-pyrimidin-4-yl)-5-(2,4,5-trifluoro-benzyloxymethyl)-pyrrolidine-3-thiol; trifluoro-acetate (1:1);
v) (3R,5S)-1-(2-Methylamino-pyrimidin-4-yl)-5-(2,4,5-trifluoro-benzyloxymethyl)-pyrrolidine-3-thiol; trifluoro-acetate (1:1);
w) (3R,5S)-1-(2-Butylamino-pyrimidin-4-yl)-5-(2,4,5-trifluoro-benzyloxymethyl)-pyrrolidine-3-thiol; trifluoro-acetate (1:1);
x) (3R,5S)-1-(2-Methylsulfanyl-pyrimidin-4-yl)-5-(2,4,5-trifluoro-benzyloxymethyl)-pyrrolidine-3-thiol;
y) (3R,5S)-1-(2-Phenoxy-pyrimidin-4-yl)-5-(2,4,5-trifluoro-benzyloxymethyl)-pyrrolidine-3-thiol;
z) (3R,5S)-1-(5-Phenyl-pyrimidin-2-yl)-5-(2,4,5-trifluoro-benzyloxymethyl)-pyrrolidine-3-thiol;
aa) (3R,5S)-1-(5-Pyridin-2-yl-pyrimidin-2-yl)-5-(2,4,5-trifluoro-benzyloxymethyl)-pyrrolidine-3-thiol; compound with trifluoro-acetic acid;
bb) (3R,5S)-1-(5-Pyridin-4-yl-pyrimidin-2-yl)-5-(2,4,5-trifluoro-benzyloxymethyl)-pyrrolidine-3-thiol;
cc) (3R,5S)-1-(5-Thiophen-3-yl-pyrimidin-2-yl)-5-(2,4,5-trifluoro-benzyloxymethyl)-pyrrolidine-3-thiol;
dd) (3R,5S)-1-[5-(4-Methoxy-phenyl)-pyrimidin-2-yl]-5-(2,4,5-trifluoro-benzyloxymethyl)-pyrrolidine-3-thiol;
ee) (2S,4R)-4-{2-[4-Mercapto-2-(2,4,5-trifluoro-benzyloxymethyl)-pyrrolidin-1-yl]-pyrimidin-5-yl}-benzoic acid;
ff) (3R,5S)-1-(5-Allyl-pyrimidin-2-yl)-5-(2,4,5-trifluoro-benzyloxymethyl)-pyrrolidine-3-thiol;
gg) (3R,5S)-1-(5-Pyridin-3-yl-pyrimidin-2-yl)-5-(2,4,5-trifluoro-benzyloxymethyl)-pyrrolidine-3-thiol; and
hh) (3R,5S)-5-(2,4,5-Trifluoro-benzyloxymethyl)-1-(5-trimethylsilanylethynyl-pyrimidin-2-yl)-pyrrolidine-3-thiol.

These compounds show $IC_{50}$ values in the radioimmunoassay (E on ECE-inhibition, see blow) of about 0.5 nM to 100 nM.

Especially preferred compounds as defined by formula (I) are those selected from the group consisting of a) (3R,5S)-1-Pyrimidin-2-yl-5-(2,4,5-trifluoro-benzyloxymethyl)-pyrrolidine-3-thiol trifluoro-acetate (1:1);
b) (3R,5S)-1-(6-Phenyl-pyridazin-3-yl)-5-(2,4,5-trifluoro-benzyloxymethyl)-pyrrolidine-3-thiol;
c) (3R,5S)-1-Pyrazin-2-yl-5-(2,4,5-trifluoro-benzyloxymethyl)-pyrrolidine-3-thiol; compound with trifluoro-acetic acid;
d) (3R,5S)-1-(5-Ethyl-pyrimidin-2-yl)-5-(2,4,5-trifluoro-benzyloxymethyl)-pyrrolidine-3-thiol trifluoro-acetate (1:1);
e) (3R,5S)-1-(5-Propyl-pyrimidin-2-yl)-5-(2,4,5-trifluoro-benzyloxymethyl)-pyrrolidine-3-thiol trifluoro-acetate (1:1);
f) (3R,5S)-5-(2,4,5-Trifluoro-benzyloxymethyl)-1-(5-trifluoromethyl-pyridin-2-yl)-pyrrolidine-3-thiol trifluoro-acetate (1:1);
g) (3R,5S)-1-(5-Phenyl-pyrimidin-2-yl)-5-(2,4,5-trifluoro-benzyloxymethyl)-pyrrolidine-3-thiol;
h) (3R,5S)-Thioacetic acid S-[1-(5-propyl-pyrimidin-2-yl)-5-(2,4,5-trifluoro-benzyloxymethyl)-pyrrolidin-3-yl] ester;
i) (3R,5S)-1-(5-Pyridin-2-yl-pyrimidin-2-yl)-5-(2,4,5-trifluoro-benzyloxymethyl)-pyrrolidine-3-thiol; compound with trifluoro-acetic acid;
j) (3R,5S)-1-(5-Pyridin-4-yl-pyrimidin-2-yl)-5-(2,4,5-trifluoro-benzyloxymethyl)-pyrrolidine-3-thiol;
k) 1-(5-Thiophen-3-yl-pyrimidin-2-yl)-5-(2,4,5-trifluoro-benzyloxymethyl)-pyrrolidine-3-thiol;
l) 1-(5-Pyridin-3-yl-pyrimidin-2-yl)-5-(2,4,5-trifluoro-benzyloxymethyl)-pyrrolidine-3-thiol;
m) (2S,4R)-5-[(2,5-Difluoro-benzylamino)-methyl]-1-(5-propyl-pyrimidin-2-yl)-pyrrolidine-3-thiol; and
n) (3R,5S)-Thioacetic acid S-[5-[(2,5-difluoro-benzylamino)-methyl]-1-(5-propyl-pyrimidin-2-yl)-pyrrolidin-3-yl]ester.

The invention also refers to pharmaceutical compositions containing a compound as defined above and a pharmaceutically acceptable excipient.

A further embodiment of the present invention refers to the use of compounds as defined above as active ingredients in the manufacture of medicaments comprising a compound as defined above for the prophylaxis and treatment of disorders which are caused by endothelin-converting enzyme (ECE) activity especially myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, graft rejection, diseases associated with cytostatic, ophthalmological, and cerebroprotective indications, and organ protection.

Further the invention refers to the use of compounds as described above for the treatment or prophylaxis of diseases which are associated with myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, graft rejection, diseases associated with cytostatic, ophthalmological, and cerebroprotective indications, and organ protection.

In addition the invention comprises compounds as described above for use as therapeutic active substances, in particular in context with diseases which are associated with zinc hydrolase activity such as myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, graft rejection, diseases associated with cytostatic, ophthalmological, and cerebroprotective indications, and organ protection.

The invention also comprises a method for the therapeutic and/or prophylactic treatment of myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, graft rejection, diseases associated with cytostatic, ophthalmological, and cerebroprotective indications, and organ protection, which method comprises administering a compound as defined above to a human being or animal.

The invention also relates to the use of compounds as defined above for the inhibition of zinc hydrolase activity.

The invention also refers to the above compounds whenever manufactured by a process as described below.

Compounds of formula (I) can be prepared by methods known in the art or as described below. Unless otherwise indicated, the substituents $R^1$, $R^2$, $R^3$ $R^4$, $R^5$, $X^1$, $X^2$, $X^3$, $X^4$, and Y mentioned below are as defined above.

The process for the preparation of a compound as defined above may comprise the reaction of a compound of formula III

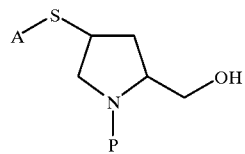

wherein A is a HS- and P is a NH-protecting group as described in the following sections, a) with a $R^2$-halogenide for introduction of a —$OR^2$ group followed by P-deprotection and introduction of a heteroaromate: or b) first P-deprotection of formula (III), introduction of a heteroaromate as defined above followed by —OH/—$NH_2$ replacement and reductive amination to introduce $R^2$;

optionally followed by conversion of a $R^1$, $R^2$, $R^3$, $R^4$ group as above into a different one and/or deprotection and/or thiol liberation.

For the preparation of compounds of formula (I) the reaction pathway of scheme 1 can be followed: the starting material is commercial available or is synthesized from hydroxyproline by methods known in the art and described for example in "The Practice of Peptide Synthesis", M. Bodanszky and A. Bodanszky, Springer Verlag, Berlin, 1984.

The synthesis starts with the inversion of the configuration via preparation of the corresponding mesylate (e.g. reaction with $MeSO_3H/Ph_3P$/DIAD in toluene at RT to 80° C.), via the chloride (e.g. reaction with $Ph_3P/CCl_4$ in $CH_2Cl_2$ at 3° C. to RT) or via the bromide (e.g. reaction with $LiBr$/DEAD/$Ph_3P$ in THF at 4° C. to RT). For retention of configuration the corresponding reaction may be performed with $MeSO_2Cl$/pyridine/DMAP at 0° C. to RT.

Step b of scheme 1 shows the introduction of the protected thio moiety, e.g. by reaction with triphenylmethanthiol or 4-methoxybenzylmercaptane (K-Ot-Bu in DMF for Cl: 0° C., for Br: 0° C. to RT, for Mes: RT to 100° C.).

Reaction of step c of scheme 1 may be performed via Method A (LAH in THF at −20° C.) or Method B (Red-Al in toluene/THF at −50° C.).

Reaction of step d (for Y=—O—) may be performed with

1. NaH/$R^2$Br in DMF 0° C. to RT, (O-alkylation)
2. TFA in $CH_2Cl_2$ −20 to RT, (BOC deprotection)
3. Method A: 2-Chloro-hetero-aromate/N-ethyldiisopropylamine 3 h 80° C., Method B (parallel-synthesis): 2-Chloro-hetero-aromate/N-ethyldiisopropylamine in dioxane or DMF, 16 h -2days 80–130° C.,Method C (for less reactive compounds): 2-Chloro-hetero-aromate/N-ethyldiisopropylamine/ CuI 10 h 80° C.

For the preparation of phenolether compounds, the corresponding reaction may be performed under Mitsunobu conditions (DEAD/$Ph_3P$/PhOH or PhSH in THF).

For Y being $NR^2$ or N-heterocycle a mesylation reaction may be performed: e.g.

1. 1.1 eq $MeSO_2Cl$/1.5pyridine/1 eq DMAP, (mesylation);
2. Y$R^2$ is e.g. pyrrole, imidazol or, 1 eq NaI, NaH in DMF 0° C. to RT;
3. $iPr_3SiH$ in TFA/$CH_2Cl_2$ or $CH_3CN$ (for trityl-thiol deprotection).

Thiol liberation may be performed with TFA/$iPr_3SiH$ in $CH_2Cl_2$ or $CH_3CN$ at RT.

An alternative route for the preparation of compounds with Y being N is: first P-deprotection (TFA in $CH_2Cl_2$ at −20° C. to RT for P=BOC), followed by reaction with 2-chloro-hetero-aromate/N-ethyldiisopropylamine/CuI for 10 h at 80° C. (step f) followed by
1. phthalimide, $DEAD/Ph_3P$ in THF 0 to 80° C., (phthalimide introduction under Mitsunobu condition)
2. hydrazine hydrate, EtOH, RT, (phthalimide deprotection) followed by reaction with the corresponding
3. aldehyde, $SnCl_2$, $NaBH_3CN$, MeOH, (reductive amination) (step g)
4. If necessary. $R^5$ may be introduced by reaction with $R^5Br/K_2CO_3$ in acetonitrile, RT, followed by reaction with
5. $iPr_3SiH$ in $TFA/CH_2Cl_2$ or $CH_3CN$ (for trityl-thiol deprotection).

3. If $XR^3$ is OMe, the reaction may be performed with 2.2 eq MeONa in MeOH at RT to 75° C. (10 h) (no 4-fluoro-replacement takes place in $YR^2$=2,4,5-trifluoro-benzyloxy ether derivatives).

4. If $XR^3$ is SMe, the reaction may be performed with 2.2 eq MeSNa/NaI in THF, RT to 70° C. for 28 h.

5. If $XR^3$ is $NHR^3$, the reaction may be performed with 7.5–30 eq $H_2NR^3/iPr_2EtN$ in dioxane at 90–105° C. for 48 h.

6. Thiol liberation may then be performed with TFA/ $iPr_3SiH$ in $CH_2Cl_2$ or $CH_3CN$ at RT (step b).

The reaction pathway of scheme 2 B shows further synthesis routes for compounds of formula (I):

SCHEME 1:

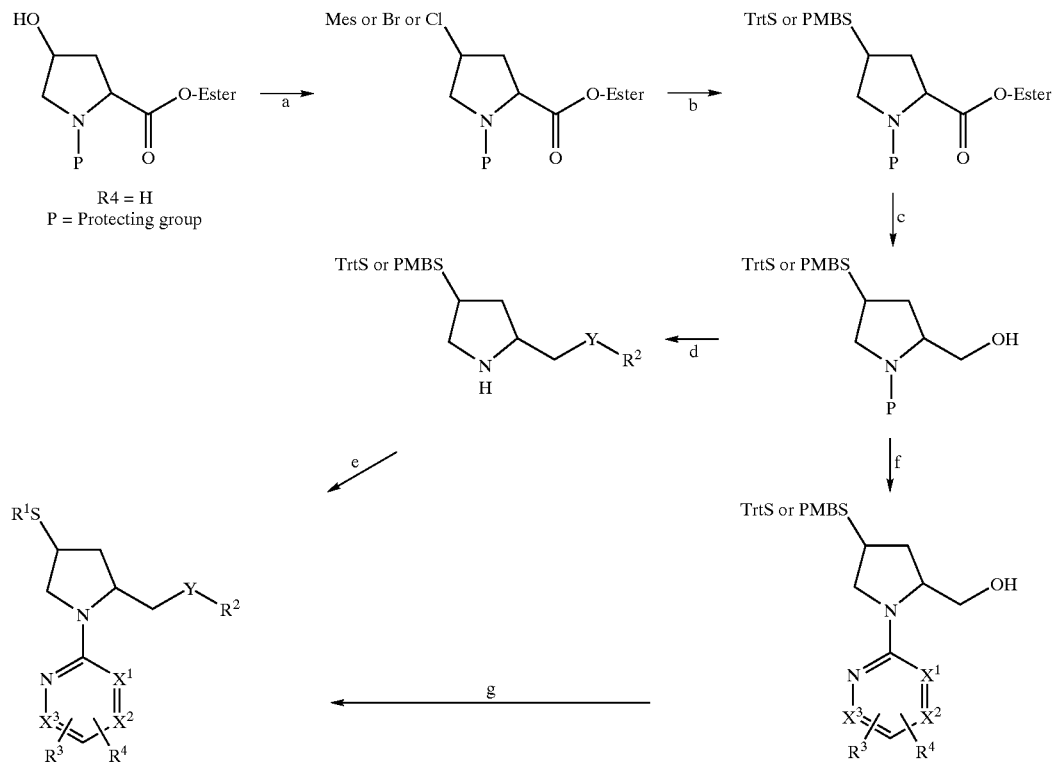

Scheme 2 summarizes special reaction pathways for the preparation of compounds of formula (I):

Scheme 2 A refers to a Cl-derivative as starting material which was synthesized as described in Scheme 1 (step e) with 2,4-dichloropyrimidine:

1. If $XR^3$ is OMe the reaction may be performed with 3 eq MeOH/NaH in DMF, RT (4-fluoro-replacement takes place in $YR^2$=2,4,5-trifluoro benzyloxy ether derivatives).
2. If $XR^3$ is OPh, the reaction may be performed with 10 eq PhOH/NaH in DMF for 8 h at 70° C.

Reaction of step c) may be performed with the following methods:
1. Suzuki-coupling with $ArylB(OH)_2/Pd(PhP)_4$ in dimethoxyethane/EtOH and 2 M $Na_2CO_3$ 2 h at 90° C.; or
2. reaction with $ArylB(OH)_2/PdCl_2(dppf)$ in dioxane and 2 M $Na_2CO_3$ for 24–48 h at 80° C.; or
3. i. synthesis of a boron ester (e.g. 4,4,5,5-Tetramethyl-2-phenyl-[1,3,2]dioxaborolane derivative) by reaction with bis(pinacolato)diboron/KOAc/$PdCl_2$(dppf) in DMF at 80° C., and
4. ii. reaction with Bromoaromat/$PdCl_2$(dppf)/2 M $Na_2CO_3$ for 16 h at 80° C.; or Sonogashira-Hagihara coupling: reaction with ethinyltrimethylsilane/$Et_3N$/ $PdCl_2(Ph_3P)2$/CuI in DMF at 80° C.

SCHEME 2:

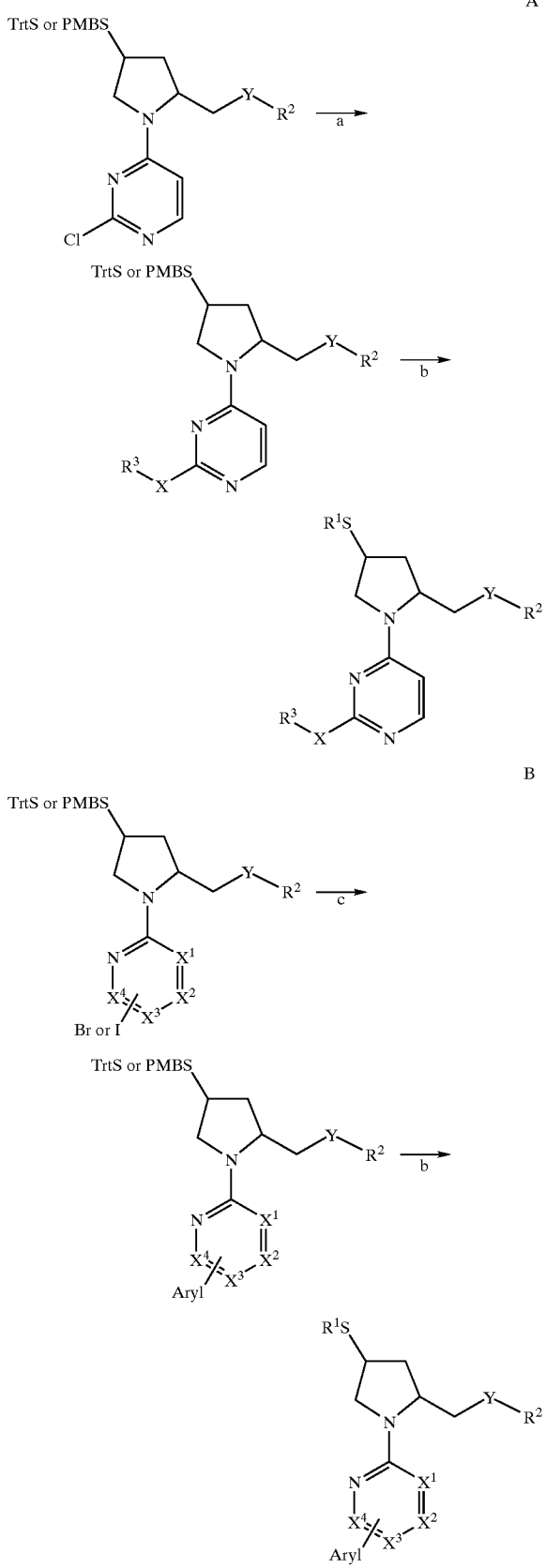

SCHEME 3:

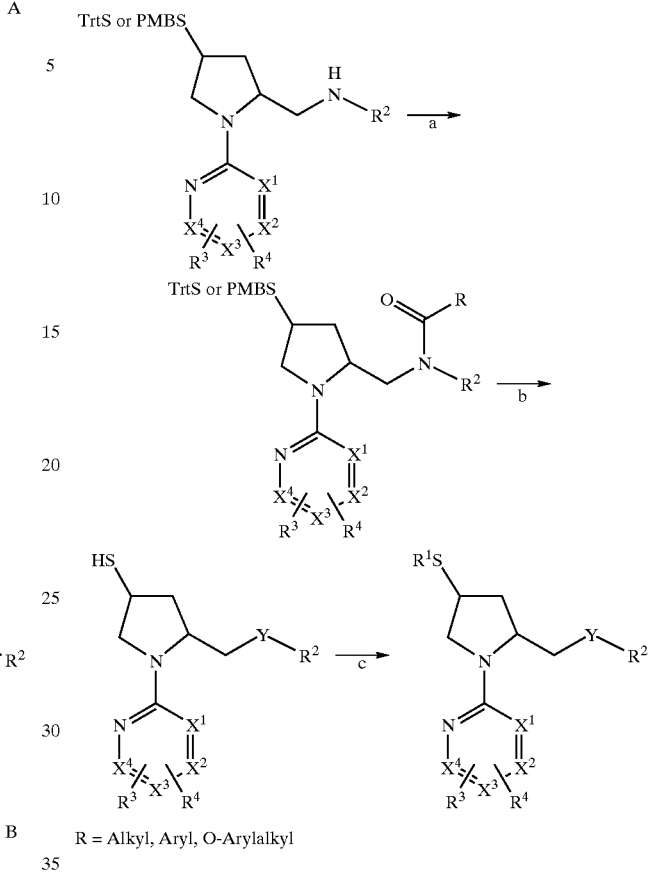

R = Alkyl, Aryl, O-Arylalkyl

Further derivatization of compounds of formula (I) is described in Scheme 3:

In case Y is nitrogen, reaction of step a may be performed with RCOCl, iPr$_2$NEt, 4-(N-Benzyl-N-methylamino) pyridine polymer-supported, CH$_2$Cl$_2$ (N-acylation) followed by reaction with iPr$_3$SiH, TFA, CH$_2$Cl$_2$, (thiol liberation). In case Y is protected nitrogen or oxygen, the reaction with the free thiol may be performed according to step c with RCOCl in pyridine at 0° C. to RT or BOC-Cys (Npys)-OH (=2-(BOC-Cys)disulfanyl-3-nitro-pyridine) in DMF/0.1 M phosphate buffer (pH 6.2). In case of Y is a benzyloxy protected nitrogen, selective deprotection with 33% HBr in acetic acid at 0° C. to RT is possible.

Dimeric forms of a compound of formula I may be prepared by oxidative treatment of the formula I monomers.

On the basis of their capability of inhibiting metalloprotease activity, especially zinc hydrolase activity, the compounds of formula I can be used as medicaments for the treatment and prophylaxis of disorders which are associated with vasoconstriction of increasing occurrences. Examples of such disorders are high blood pressure, coronary disorders, cardiac insufficiency, renal and myocardial ischaemia, renal insufficiency, dialysis, cerebral ischaemia, cardiac infarct, migraine, subarachnoid haemorrhage, Raynaud syndrome and pulmonary high pressure. They can also be used in atherosclerosis, the prevention of restenosis after balloon-induced vascular dilation, inflammations, gastric and duodenal ulcers, ulcus cruris, gram-negative sepsis, shock, glomerulonephtritis, renal colic, glaucoma, asthma, in the therapy and prophylaxis of diabetic complications and complications in the administration of cyclosporin, as well as other disorders associated with endothelin activities.

The ability of the compounds of formula (I) to inhibit metalloprotease activity, particularly zinc hydrolase activity, maybe demonstrated by a variety of in vitro and in vivo assays known to those of ordinary skill in the art. Pharmaceutically acceptable esters, pharmaceutically acceptable salts and dimeric forms of the compounds of formula I can also be tested by those of ordinary skill in the art for their ability to inhibit metalloprotease activity.

A) Cell Culture

A stable human umbilical vein endothelial cell line (ECV304) was cultured in "cell factories" as described until confluency (Schweizer et al. 1997, Biochem. J. 328: 871–878). At confluency cells were detached with a trypsin/EDTA solution and collected by low speed centrifugation. The cell pellet was washed once with phosphate buffered saline pH 7.0 and stored at −80° C. until use.

B) Solubilization of ECE from ECV304 Cells

All procedures were performed at 0–4° C. if not stated otherwise. The cell pellet of $1\times10^9$ cells was suspended in 50 ml of buffer A (20 mM Tris/HCl, pH 7.5 containing 5 mM $MgCl_2$, 100 µM PMSF, 20 µM E64, 20 µM leupeptin) and sonicated. The resulting cell homogenate was centrifuged at 100,000 $g_{av}$ for 60 minutes. The supernatant was discarded and the resulting membrane pellet was homogenized in 50 ml buffer A and centrifugated as described. The washing of the membrane fraction in buffer A was repeated twice. The final membrane preparation was homogenized in 50 ml of buffer B (buffer A+0.5% Tween 20 (v/v), 0.5% CHAPS (w/v), 0.5% Digitonin (w/v)) and stirred at 4° C. for 2 hours. Thereafter the remaining membrane fragments were sedimented as described. The resulting clear supernatant containing the solubilized ECE was stored in 1.0 ml aliquots at −120° C. until use.

C) ECE Assay

The assay measured the production of ET-1 from human big ET-1. To measure high numbers of samples an assay performed in 96 well plates was invented. The enzyme reaction and the radioimmunological detection of the produced ET-1 was performed in the same well, using a specifically developed and optimized coating technique.

D) Coating of Plates

Fluoronunc Maxisorp White (code 437796) 96 well plates were irradiated with 1 joule for 30 minutes in a UV Stratalinker 2400 (Stratagene). The 96 well plates were then fill with 300 µl protein A solution (2 µg/ml in 0.1 M $Na_2CO_3$ pH 9.5) per well and incubated for 48 hours at 4° C. Coated plates can be stored for up to 3 weeks at 4° C. until use.

Before use the protein A solution is discarded and the plates are blocked for 2 hours at 4° C. with 0.5% BSA in 0.1M $Na_2CO_3$, pH 9.5.

Plates were washed with bidestilled water and were ready to perform the ECE assay.

E) Screening Assay

Test compounds are solved and diluted in DMSO. 10 µl of DMSO was placed in the wells, followed by 125 µl of assay buffer (50 mM Tris/HCl, pH 7.0, 1 µM Thiorphan, 0,1% $NaN_3$, 0.1% BSA) containing 200 ng big ET-1. The enzyme reaction was started by the addition of 50 µl of solubilized ECE (diluted in assay buffer 1:30 to 1:60 fold (v/v)). The enzyme reaction was carried out for 30 minutes at 37° C. The enzyme reaction was stopped by addition of 10 µl 150 mM ETDA, pH 7.0.

Radioimmunoassay

The ET-1 RIA was performed principally as described earlier (Löffler, B.-M. and Maire, J.-P. 1994, Endothelium 1: 273–286). To plates containing the EDTA stopped enzyme reaction mixture 25 µl of assay buffer containing 20000 cpm (3-($^{125}$I)Tyr)-endothelin-1 and 25 µl of the ET specific antiserum AS-3 (dilution in assay buffer 1:1000) was added. Plates were incubated under mixing at 4° C. over night. Thereafter, the liquid phase was sucked with a plate washer and plates were washed once with bidestilled water. To the washed plates 200 µl scintillation cocktail (Microscint 40 LSC-Cocktail, Packard, code 6013641) was added and plates were counted for 2 minutes per well in a Topcount.

Standard curves were prepared in plates with synthetic ET-1 with final concentrations of 0 to 3000 pg ET-1 per well. In all plates controls for maximal ECE activity (in the presence of 10 µl DMSO) and for background production of ET-1 immunoreactivity (in the presence of 10 mM EDTA or 100 µM phosphoramidon) were performed. Assays were run in triplicate.

F) Kinetic Assay

The described assay format could be used to determine the kinetic characteristics of the used ECE preparation as well as different ECE inhibitors (i.e. Km, Ki) by variation of the substrate concentration used in the assay.

G) Cell based ECE Assay

Human ECE-1c was stable expressed in MDCK cells as described (Schweizer et al. 1997, Biochem. J. 328: 871–878). Cells were cultured in 24 well plates to confluency in Dulbecco's modified Eagles's medium (DMEM) supplemented with 10% (v/v) fetal bovine serum (FBS), 0.8 mg/ml geneticin, 100 i.u./ml penicillin and 100 µg/ml streptomycin in a humidified air/$CO_2$ (19:1) atmosphere. Before ECE assay the medium was replaced by 0.5 ml DMEM-HBSS 1:1, 10 mM HEPES pH 7.0 supplemented with 0.1% (w/v) BSA. The inhibitors were added in DMSO at a final concentration of 1%. The enzyme reaction was started by the addition of 0.42 µM human big ET-1 and performed for 1.5 hours at 37° C. in an incubator. At the end of incubation, the incubation medium was quickly removed and aliquots were analysed by radioimmunoassay for produced ET-1 as described above.

The ECE screening assay was validated by the measurement of the characteristic inhibitor constants of phosphoramidon ($IC_{50}$ 0.8±0.2 µM) and CGS 314447 ($IC_{50}$ 20±4 nM) [De Lombaert, Stephane; Stamford, Lisa B.; Blanchard, Louis; Tan, Jenny; Hoyer, Denton; Diefenbacher, Clive G.; Wei, Dongchu; Wallace, Eli M.; Moskal, Michael A.; et al. Potent non-peptidic dual inhibitors of endothelin-converting enzyme and neutral endopeptidase 24.11. Bioorg. Med. Chem. Lett. (1997), 7(8), 1059–1064]. The two inhibitors were measured with $IC_{50}$ values not significantly different from those described in the literature but measured with different assay protocols. In the cell based assay phosphoramidon showed an $IC_{50}$ of 4 µM. This assay gave additional information about the inhibitory potency of inhibitors under much more physiologic conditions, as e.g. the ECE was embedded in a normal plasma membrane environment. It is important to state, that the screening assay was performed in the presence of 1 µM Thiorphan to block any potential big ET-1 degradation due to the action of NEP24.11. No NEP activity was present in MDCK-ECE-1c transfected cells in preliminary experiments when ET-1 production was measured in presence or absence of thiorphan. In subsequent experiments no thiorphan was added in the incubation medium.

According to the above methods, the compounds of the present invention show $IC_{50}$ values in the radioimmunoassay (E on ECE-inhibition) of about 0.5 nM to about 100 µM. The preferred compounds show values of 0.5 nM to 100 nM.

As mentioned earlier, medicaments containing a compound of formula I are also an object of the present invention as is a process for the manufacture of such medicaments, which process comprises bringing one or more compounds of formula I and, if desired, one or more other therapeutically valuable substances into a galenical administration form.

The pharmaceutical compositions may be administered orally, for example in the form of tablets, coated tablets, dragees, hard or soft gelatin capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragees or hard gelatin capsules the compounds of the present invention may be admixed with pharmaceutically inert, inorganic or organic excipients. Examples of suitable excipients for tablets, dragees or hard gelatin capsules include lactose, maize starch or derivatives thereof, talc or stearic acid or salts thereof.

Suitable excipients for use with soft gelatin capsules include for example vegetable oils, waxes, fats, semi-solid or liquid polyols etc.; according to the nature of the active ingredients it may however be the case that no excipient is needed at all for soft gelatin capsules.

For the preparation of solutions and syrups, excipients which may be used include for example water, polyols, saccharose, invert sugar and glucose. For injectable solutions, excipients which may be used include for example water, alcohols, polyols, glycerin, and vegetable oils. For suppositories, and local or percutaneous application, excipients which may be used include for example natural or hardened oils, waxes, fats and semi-solid or liquid polyols.

The pharmaceutical compositions may also contain preserving agents, antioxidants, solubilising agents, stabilizing agents, wetting agents, emulsifiers, sweeteners, colorants, odorants, salts for the variation of osmotic pressure, buffers, coating agents or antioxidants. They may also contain other therapeutically valuable agents.

The dosages in which the compounds of formula I are administered in effective amounts depend on the nature of the specific active ingredient, the age and the requirements of the patient and the mode of application. In general, dosages of 0.1–100 mg/kg body weight per day come into consideration, although the upper limit quoted can be exceeded when this is shown to be indicated.

The following specific examples are provided as a guide to assist in the practice of the invention, and are not intended as a limitation on the scope of the invention.

EXAMPLES

All reactions are done under argon.

A) Abbreviations

EtOAc ethylacetate, EtOH ethanol, THF tetrahydrofurane, $Et_2O$ diethylether, MeOH methanol, $CH_2Cl_2$ dichloromethane, DMF dimethylformamide, BOC t-butyloxycarbonyl, LAH Lithium aluminium hydride, LDA lithium diisopropylamide, DEAD Diethyl azodicarboxylate, DIAD Diisopropyl azodicarboxylate, DMAP 4-Dimethylamino-pyridine, $iPr_2NEt$ N-ethyldiisopropylamine, $Ph_3P$ triphenylphosphine, Red-Al solution Natrium-dihydrido-bis-(2-methoxyethoxy)-aluminat-solution, $Et_3N$ triethylamine, $ArylB(OH)_2$=aryl-, heteroaryl-, alpha-alkenyl boronic acid, $PdCl_2(dppf)(1,1'$-bis (diphenylphosphino)ferrocene)dichloropalladium (II). $CH_2Cl_2$ (1:1), $Pd(Ph_3P)_4$ tetrakis(triphenylphosphine) palladium, $iPr_3SiH$ triisopropylsilane, $PdCl_2(Ph_3P)_2$ bis (triphenylphosphine) palladium(II) dichloride, $Et_3SiH$ triethylsilane, TFA trifluoroacetic acid.

B) General Method for a Selective BOC-deprotection

A solution of 15.1 mmol N-BOC-S-Trityl compound in 30 ml $CH_2Cl_2$ was treated at −20° C. with 34 ml TFA and warmed up to room temperature during 5.5 h. The reaction was evaporated and treated with aqueous saturated $NaHCO_3$ solution/EtOAc (3×) to give the free aminotritylsulfanyl.

C) General Method for Ester Hydrolysis

A solution of 5.38 mmol carboxylic acid methyl ester was dissolved in 150 ml EtOH and treated at RT with 10.8 ml (10.8 mmol) aqueous 1 N NaOH. After 3 h the reaction was evaporated and poured into aqueous 10% $KHSO_4$/EtOAc (3×). The organic phases were washed with aqueous 10% NaCl solution and dried over $Na_2SO_4$ to give the carboxylic acid.

D) General Method for S-deprotection

Trityl Deprotection with Triisopropylsilane: A solution of 2.84 mmol trityl-protected compound in 30 ml $CH_2Cl_2$ was treated at 0° C. with 8 ml TFA and 5.82 ml (28 mmol) triisopropylsilane. After 30 min at RT the solution was completely evaporated and the compound precipitated twice from $Et_2O$/pentane or purified by silcagel with cyclohexane, cyclohexane/EtOAc 9:1 to 1:1 as eluent to give the thiol trifluoro-acetate (1:1) as colourless oil.

E) General Method for S-deprotection Modified 1 eq trytilated educt in $CH_2Cl_2$ (20 ml/mmol) was treated with 10–20 eq triisopropyl silane and 10–20 eq TFA at 0° C. The solution was stirred at 0° C. until no educt was detected, was poured on sat. $NaHCO_3$ solution and was extracted with $CH_2Cl_2$. The combined organic phases were washed with brine and are dried over $Na_2SO_4$.

Example 1

Starting Materials

The starting material: (2S,4R)-4-tritylsulfanyl-pyrrolidine-1,2-dicarboxylic acid 1-tert-butyl ester 2-methyl ester for the synthesis of the compound of the present invention are known in the art and described for example in International Patent Application WO98/20001 and European Patent Application Publication No. EP-A-696593.

1.1 (2S,4S)-4-Chloro-pyrrolidine-1,2-dicarboxylic acid 1-tert-butyl ester 2-methyl ester A solution of 374 g (1.48 mol) (2S,4R)-4-Hydroxy-pyrrolidine-1,2-dicarboxylic acid 1-tert-butyl ester 2-methyl ester in 1.6 l $CH_2Cl_2$ was treated with 680 g (2.6 mol) triphenylphosphine, cooled to 3–5° C. and treated in 10 min with 1.241 (12.8 mol) $CCl_4$, after 2 h at this temperature cooling was stopped, the reaction raised during 2 h to 35° C. It was cooled down to 20° C. and stirred for further 45 min. After addition of 4 l of n-heptane, the reaction was evaporated to 2.9 l, cooled to 0° C., filtered, the residue was treated twice the same way, the third time by dissolving the residue again in 2 l of $CH_2Cl_2$. The solvents were evaporated and filtered through silica gel with hexane/tert.-butyl-methylether 9:1 as eluent. Evaporation of the solvents gave 347 g (89%) of (2S,4S)-4-Chloro-pyrrolidine-1,2-dicarboxylic acid 1-tert-butyl ester 2-methyl ester, MS: 246 ($MH^+$).

1.2 (2S,4R)-4-Tritylsulfanyl-pyrrolidine-1,2-dicarboxylic acid 1-tert-butyl ester 2-methyl ester A solution of 76 g (0.68 mol) potassium-tert.-butylate in 1.5 l DMF was cooled (−3° C.) and treated slowly (1.5 h) with 202 g (0.73 mol) triphenylmethanethiol in 0.8 l DMF (at max 1° C.). After 2.5 h at 0° C., a solution of 161 g (0.61 mol) of (2S,4S)-4-Chloro-pyrrolidine-1,2-dicarboxylic acid 1-tert-butyl ester 2-methyl ester in 0.35 l DMF was added. The reaction was stirred over night at 2° C., evaporated, dissolved in 1.5 l EtOAc, poured into 2.7 l aqueous saturated $NH_4Cl$ solution and extracted with EtOAc (2×). The organic phase was washed with aqueous saturated $NaHCO_3$, dried over $Na_2SO_4$ and evaporated. Colum chromatographyon silica gel with hexane/EtOAc (95:5 to 7:3) gave 268 g (87%) (2S,4R)-4-Tritylsulfanyl-pyrrolidine-1,2-dicarboxylic acid 1-tert-butyl ester 2-methyl ester, MS: 504 ($MH^{30}$).

1.3 Ester Reduction

A) (2S,4R)-2-Hydroxymethyl-4-tritylsulfanyl-pyrrolidine-1-carboxylic acid Tert-butyl ester A solution of 35 g (69 mmol) (2S,4R)-4-Tritylsulfanyl-pyrrolidine-1,2-dicarboxylic acid 1-tert-butyl ester 2-methyl ester in 380 ml toluene/60 ml THF was treated at −47° C. to −50° C. with 44 g (152 mmol) of a 70% solution of sodium dihydrido-bis(2-methoxy-ethoxo)aluminate in toluene (3.5 M Red-Al in toluene). After 3 h at −50° C. and 1 h at −30° C. the solution was poured into water (1 l) with 40 g of citric acid and extracted with EtOAc (2×). The organic phase was dried over $Na_2SO_4$ and evaporated. Column chromatography on silica gel with hexane/EtOAc (7:3) gave 23.0 g (69%) (2S,4R)-2-Hydroxymethyl-4-tritylsulfanyl-pyrrolidine-1-carboxylic acid tert-butyl ester, MS: 476 (MH+).

B) (2S,4R)-2-(2,4,5-Trifluoro-benzyloxymethyl)-4-tritylsulfanyl-pyrrolidine-1-carboxylic acid Tert-butyl ester A solution of 15.5 g (32.59 mmol) (2S,4R)-2-Hydroxymethyl-4-tritylsulfanyl-pyrrolidine-1-carboxylic acid tert-butyl ester and 24.7 g (109.77 mmol) 2,4,5-trifluoro-benzylbromide in 700 ml DMF at 0° C. was treated with 2.28 g (52.14 mmol) of 55% NaH in 4 portions and warmed up to RT during 7 h. The reaction was cooled to 0° C. and treated with 500 ml aqueous saturated $NH_4Cl$ solution, extracted with EtOAc (3×). The organic phase was washed with 10% NaCl dried over $Na_2SO_4$ and evaporated. Flash column chromatography on silica gel with hexane/EtOAc (9:1 to 8.5:1.5) gave 9.37 g (46%) of (2S,4R)-2-(2,4,5-Trifluoro-benzyloxymethyl)-4-tritylsulfanyl-pyrrolidine-1-carboxylic acid tert-butyl ester, MS: 620 ($MH^+$).

C) (2S,4R)-2-(2,4,5-Trifluoro-benzyloxymethyl)-4-tritylsulfanyl-pyrrolidine

A solution of 9.37 g (15.11 mmol) (2S,4R)-2-(2,4,5-Trifluoro-benzyloxymethyl)-4-tritylsulfanyl-pyrrolidine-1-carboxylic acid tert-butyl ester in 30 ml $CH_2Cl_2$ was treated at −20° C. with 34 ml TFA and warmed up to RT during 5.5 h. The reaction was evaporated and treated with aqueous sat $NaHCO_3$ solution/EtOAc (3×) to give 7.77 g (quantitative) (2S,4R)-2-(2,4,5-Trifluoro-benzyloxymethyl)-4-tritylsulfanyl-pyrrolidine, MS: 520 (M).

Example 2

N-Pyrrolidine Derivatives (Scheme 2)

2.1 Method A

A mixture of 2.08 g (4 mmol)(2S,4R)-2-(2,4,5-Trifluoro-benzyloxymethyl)-4-tritylsulfanyl-pyrrolidine, 0.687 g (6 mmol) 2-chloropyrimidine and 1.16 ml (6.8 mmol) N-ethyldiisopropylamine was heated for 3 h at 80° C. The reaction was cooled and partitioned between $H_2O/Et_2O$ (3×300). The organic phases were washed with aqueous saturated $NaHCO_3$, aqueous 10% NaCl, dried ($NaSO_4$) and evaporated. Flash chromatography on silica gel ($CH_2Cl_2$/EtOAc 97.5:2.5) gave 1.7 g (71%) (2S,4R)-2-[2-(2,4,5-Trifluoro-benzyloxymethyl)-4-tritylsulfanyl-pyrrolidin-1-yl]-pyrimidine, MS: 598 ($MH^+$).

In analogy:

a) (2S,4R)-2-(2,4,5-Trifluoro-benzyloxymethyl)-4-tritylsulfanyl-pyrrolidine and 2,4-dichloropyrimidine gave (2S,4R)-2-Chloro-4-[2-(2,4,5-trifluoro-benzyloxymethyl)-4-tritylsulfanyl-pyrrolidin-1-yl]-pyrimidine, MS: 632 ($MH^+$);

b) (2S,4R)-2-(2,4,5-Trifluoro-benzyloxymethyl)-4-tritylsulfanyl-pyrrolidine and 2,5-dibromo-primidine [Brown, Desmond J.; Arantz, B. W., Pyrimidine reactions. XXII. Relative reactivities of corresponding chloro-, bromo-, and iodopyrimidines in aminolysis. J. Chem. Soc. C (1971), Issue 10, 1889–91] gave (2S,4R)-5-Bromo-2-[2-(2,4,5-trifluoro-benzyloxymethyl)-4-tritylsulfanyl-pyrrolidin-1-yl]-pyrimidine, MS: 676 ($MH^+$, 1Br);

c) (2S,4R)-2-(2,4,5-Trifluoro-benzyloxymethyl)-4-tritylsulfanyl-pyrrolidine and methyl-2-chloro-6-methylpyrimidine gave (2S,4R)-6-Methyl-2-[2-(2,4,5-trifluoro-benzyloxy-methyl)-4-tritylsulfanyl-pyrrolidin-1-yl]-pyrimidine-4-carboxylic acid methyl ester, MS: 670 ($MH^+$);

d) (2S,4R)-6-Methyl-2-[2-(2,4,5-trifluoro-benzyloxymethyl)-4-tritylsulfanyl-pyrrolidin-1-yl]-pyrimidine-4-carboxylic acid methyl ester was hydrolyzed following the general method for hydrolysis of an ester (ETOH/dioxane) to give (2S,4R)-6-Methyl-2-[2-(2,4,5-trifluoro-benzyloxymethyl)-4-tritylsulfanyl-pyrrolidin-1-yl]-pyrimidine-4-carboxylic acid, MS: 656 ($MH^+$).

2.2 S-Deprotection, Method D)

A solution of 1.7 g (2.84 mmol) (2S,4R)-2-[2-(2,4,5-Trifluoro-benzyloxymethyl)-4-tritylsulfanyl-pyrrolidin-1-yl]-pyrimidine in 30 ml $CH_2Cl_2$ was treated at 0° C. with 8 ml TFA and 5.82 ml (28 mmol) triisopropylsilane. After 30 min at RT the solution was completely evaporated and the compound precipitated twice from $Et_2O$/pentane to give 1.06 g (80%) (3R,5S)-1-pyrimidin-2-yl-5-(2,4,5-trifluoro-benzyloxymethyl)-pyrrolidine-3-thiol trifluoro-acetate (1:1) as colourless oil, MS: 356 ($MH^+$).

In analogy:

a) (2S,4R)-2-Chloro-4-[2-(2,4,5-trifluoro-benzyloxymethyl)-4-tritylsulfanyl-pyrrolidin-1-yl]-pyrimidine gave (3R,5S) 1-(2-Chloro-pyrimidin-4-yl)-5-(2,4,5-trifluoro-benzyloxymethyl)-pyrrolidine-3-thiol; compound with trifluoro-acetic acid, MS: 390 ($MH^+$);

b) (2S,4R)-5-Bromo-2-[2-(2,4,5-trifluoro-benzyloxymethyl)-4-tritylsulfanyl-pyrrolidin-1-yl]-pyrimidine gave (2S,4R)-1-(5-Bromo-pyrimidin-2-yl)-5-(2,4,5-trifluoro-benzyloxymethyl)-pyrrolidine-3-thiol, MS: 434 ($MH^+$, 1Br). (nicht in Liste vorne);

c) (2S,4R)-6-Methyl-2-[2-(2,4,5-trifluoro-benzyloxymethyl)-4-tritylsulfanyl-pyrrolidin-1-yl]-pyrimidine-4-carboxylic acid gave (2S,4R)-2-[4-Mercapto-2-(2,4,5-trifluoro-benzyloxymethyl)-pyrrolidin-1-yl]-6-methyl-pyrimidine-4-carboxylic acid, MS: 414 ($MH^+$).

2.3 Method B (Synthesis in Parallel)

A solution of 0.45 mmol (2S,4R)-2-(2,4,5-Trifluoro-benzyloxymethyl)-4-tritylsulfanyl-pyrrolidine in 1 ml dioxane or 0.1 ml DMF, 2.25 mmol of 2-chloro-hetero-aromate and 2.25 mmol N-ethyldiisopropylamine was heated for 16 h-2 days at 80–130° C. (see table 1). The reaction was purified by preparative HPLC (RP-18, MeCN/H2O, UV 230 nm).

TFA/triisopropylsilane deprotection as described (see General method for S-deprotection, Method D) gave the free thiol.

2.4 Method C

A mixture of 2 g (3.85 mmol)(2S,4R)-2-(2,4,5-Trifluoro-benzyloxymethyl)-4-tritylsulfanyl-pyrrolidine, 1.2 g (7.7 mmol) 2-chloro5-n-propylpyrimidine, 1.98 ml (11.55 mmol) N-ethyldiisopropylamine and a catalytic amount of copper (I) iodide was heated for 10 h at 80° C. The reaction was cooled and partitioned between $H_2O/Et_2O$ (3×300). The organic phases were washed with aqueous saturated $NaHCO_3$, aqueous 10% NaCl, dried ($NaSO_4$) and evaporated. Flash chromatography on silica gel (toluene/$Et_2O$ 99:1) gave 2 g (81%) (2S,4R)-5-Propyl-2-[2-(2,4,5-trifluoro-benzyloxymethyl)-4-tritylsulfanyl-pyrrolidin-1-yl]-pyrimidine, MS: 640 ($MH^+$).

TFA/triisopropylsilane deprotection as described (see General method for S-deprotection, Method D) gave (3R, 5S)-1-(5-Propyl-pyrimidin-2-yl)-5-(2,4,5-trifluoro-benzyloxymethyl)-pyrrolidine-3-thiol trifluoro-acetate (1:1), MS: 398 ($MH^+$).

According to an analogous method the following compounds were prepared via reaction of (2S,4R)-2-(2,4,5-Trifluoro-benzyloxymethyl)-4-tritylsulfanyl-pyrrolidine with the 2.educt mentioned in the following table 1.

TABLE 1

By the reaction of (2S,4R)-2-(2,4,5-Trifluoro-benzyloxymethyl)-4-tritylsulfanyl-pyrrolidine 66-7030 with the 2.educt.

| NAME | 2. Educt | Method | Solvent/Time/Temp./° C. | MS | |
|---|---|---|---|---|---|
| (3R,5S)-1-(4,6-Dimethoxy-pyrimidin-2-yl)-5-(2,4,5-trifluoro-benzyloxymethyl)-pyrrolidine-3-thiol | 2-CHLORO-2,4-DIMETHOXY-PYRIMIDINE | B | DMF cat KI/16 h/80 | 416 | M+H+ |
| (3R,5S)-1-(4-Amino-5-fluoro-pyrimidin-2-yl)-5-(2,4,5-trifluoro-benzyloxy-methyl)-pyrrolidine-3-thiol | 4-AMINO-2-CHLORO-5-FLUORO-PYRIMIDINE | B | DMF/24 h/120 | 389 | M+H+ |
| 2-[(2S,4R)-4-Mercapto-2-(2,4,5-trifluoro-benzyloxy-methyl)-pyrrolidin-1-yl]-4-trifluoromethyl-pyrimidine-5-carboxylic acid methyl ester | METHYL 2-CHLORO-4-(TRIFLUORO-METHYL) PYRIMIDINE-5-CARBOXYLATE | B | no/16 h/80 | 482 | M+H+ |
| 2-[(2S,4R)-4-Mercapto-2-(2,4,5-trifluoro-benzyloxy-methyl)-pyrrolidin-1-yl]-6-methyl-pyrimidine-4-carboxylic acid methyl ester | METHYL 2-CHLORO-6-METHYL-PYRIMIDINE-4-CARBOXYLATE | B | no/16 h/80 | 428 | M+H+ |
| (3R,5S)-1-(5-Ethyl-pyrimidin-2-yl)-5-(2,4,5-trifluoro-benzyloxy-methyl)-pyrrolidine-3-thiol trifluoro-acetate (1:1) | 2-CHLORO-5-ETHYL-PYRIMIDINE | C | no/10 h/80 | 384 | M+H+ |
| (3R,5S)-5-(2,4,5-Trifluoro-benzyloxy-methyl)-1-(4-trifluoro-methyl-pyrimidin-2-yl)-pyrrolidine-3-thiol trifluoro-acetate (1:1) | 2-CHLORO-4-(TRIFLUOROMETHYL) PY-RIMIDINE | B | no/16 h/85 | 424 | M+H+ |
| 2-[(2S,4R)-4-Mercapto-2-(2,4,5-trifluoro-benzyloxymethyl)-pyrrolidin-1-yl]-nicotinonitrile | 2-CHLORO-NICOTINO-NITRILE | B | no/16 h/80 | 380 | M+H+ |
| 2-[(2S,4R)-4-Mercapto-2-(2,4,5-trifluoro-benzyloxymethyl)-pyrrolidin-1-yl]-nicotinic acid | 2-CHLORO-NICOTINIC ACID | B | dioxane, DMF/24 h/120 | 399 | M+H+ |
| 2-[(2S,4R)-4-Mercapto-2-(2,4,5-trifluoro-benzyloxymethyl)-pyrrolidin-1-yl]-nicotinamide | 2-CHLORO-NICOTIN-AMIDE | B | dioxane/16 h/80 | 398 | M+H+ |
| (3R,5S)-5-(2,4,5-Trifluoro-benzyloxy-methyl)-1-(5-trifluoro-methyl-pyridin-2-yl)-pyrrolidine-3-thiol trifluoro-acetate(1:1) | 2-CHLORO-5-(TRIFLUORO METHYL) PYRIDINE | B | no/16 h/80 | 423 | M+H+ |
| (3R,5S)-1-Pyridin-2-yl-5-(2,4,5-trifluoro-benzyloxymethyl)-pyrrolidine-3-thiol trifluoro-acetate(1:1) | 2-CHLORO-PYRIDINE | B | no/2 days/130 | 355 | M+H+ |
| (3R,5S)-1-Pyrazin-2-yl-5-(2,4,5-trifluoro-benzyloxymethyl)-pyrrolidine-3-thiol; compound with trifluoro-acetic acid | 2-CHLORO-PYRAZINE | C | no/45 min/160 | 470 | M+H+ |
| (3R,5S)-1-(6-Phenyl-pyridazin-3-yl)-5-(2,4,5-trifluoro-benzyloxy methyl)-pyrrolidine-3-thiol | 3-CHLORO-6-PHENYL-PYRIDAZINE | B | DMF/16 h/80 | 432 | M+H+ |

Example 3

Substitution on 2-Chloropyrimidine

3.1 Reaction in DMF

A solution of 0.24 (0.4 mmol) (2S,4R)-2-Chloro-4-[2-(2,4,5-trifluoro-benzyloxymethyl)-4-tritylsulfanyl-pyrrolidin-1-yl]-pyrimidine in 8 ml DMF was treated at 0° C. with 0.05 ml (1.2 mmol) MeOH and 0.054 g (1.24 mmol) 55% NaH. The reaction was kept at this temperature (6 h) and warmed up over night to RT. After extraction with aqueous saturated $NH_4Cl/Et_2O$ (3×), the organic phases were washed with aq. 10% NaCl, dried ($Na_2SO_4$) and evaporated. Flash chromatography ($CH_2Cl_2$ EtOAc 95:5) gave 0.14 g (54%) (2S,4R)-4-[2-(2,5-Difluoro-4-methoxy-benzyloxymethyl)-4-tritylsulfanyl-pyrrolidin-1-yl]-2-methoxy-pyrimidine, MS: 640 ($MH^+$). TFA/triisopropylsilane deprotection, (see General method for S-deprotection, Method D) gave (3R,5S)-5-(2,5-Difluoro-4-methoxy-benzyloxymethyl)-1-(2-methoxy-pyrimidin-4-yl)-pyrrolidine-3-thiol, MS: 398 ($MH^+$).

In analogy:

a) 2S,4R)-2-Chloro-4-[2-(2,4,5-trifluoro-benzyloxymethyl)-4-tritylsulfanyl-pyrrolidin-1-yl]-pyrimidine and 10 eq phenol/NaH after 8 h at 70° C. gave 2-Phenoxy-4-[(2S,4R)-2-(2,4,5-trifluoro-benzyloxymethyl)-4-tritylsulfanyl-pyrrolidin-1-yl]-pyrimidine, MS: 690 ($MH^+$), which was deprotected (see General method for S-deprotection, Method D) to give (3R,5S)-1-(2-Phenoxy-pyrimidin-4-yl)-5-(2,4,5-trifluoro-benzyloxymethyl)-pyrrolidine-3-thiol, MS: 448 ($MH^+$).

3.2 Reaction in Other Solvents

A solution of 0.24 (0.4 mmol) (2S,4R)-2-Chloro-4-[2-(2,4,5-trifluoro-benzyloxymethyl)-4-tritylsulfanyl-pyrrolidin-1-yl]-pyrimidine in 1 ml MeOH was treated at 0° C. with 0.16 ml (0.88 mmol) sodium methylate (5.5 M in MeOH) and kept at this temperature (2 h), warmed up and heated for 10 h at 75° C. After evaporation and extraction with aqueous saturated $NH_4Cl/Et_2O$ (3×), the organic phases were washed with aq. 10% NaCl, dried ($Na_2SO_4$) and evaporated to give 0.19 g (77%) 2-Methoxy-4-[(2S,4R)-2-(2,4,5-trifluoro-benzyloxymethyl)-4-tritylsulfanyl-pyrrolidin-1-yl]-pyrimidine, MS: 628 ($MH^+$), which was deprotected (see General method for S-deprotection, Method D) to give (3R,5S)-1-(2-Methoxy-pyrimidin-4-yl)-5-(2,4,5-trifluoro-benzyloxymethyl)-pyrrolidine-3-thiol, MS: 386 ($MH^+$).

In analogy:

a) (2S,4R)-2-Chloro-4-[2-(2,4,5-trifluoro-benzyloxymethyl)-4-tritylsulfanyl-pyrrolidin-1-yl]-pyrimidine and 2.2 eq sodium methanethiolate/2 eq sodium iodide in THF (28 h at 70° C.) gave after deprotection (see General method for S-deprotection, Method D) (3R,5S)-1-(2-Methylsulfanyl-pyrimidin-4-yl)-5-(2,4,5trifluoro-benzyloxymethyl)-pyrrolidine-3-thiol, MS: 402 ($MH^+$);

b) (2S,4R)-2-Chloro-4-[2-(2,4,5-trifluoro-benzyloxymethyl)-4-tritylsulfanyl-pyrrolidin-1-yl]-pyrimidine and 10 eq aniline/3.5 eq N-ethyldiisopropylamine in dioxane (48 h at 105° C.) gave after deprotection (see General method for S-deprotection, Method D) (3R,5S)-1-(2-Phenylamino-pyrimidin-4-yl)-5-(2,4,5-trifluoro-benzyloxymethyl)-pyrrolidine-3-thiol trifluoro-acetate (1:1), MS: 447 ($MH^+$);

c) (2S,4R)-2-Chloro-4-[2-(2,4,5-trifluoro-benzyloxymethyl)-4-tritylsulfanyl-pyrrolidin-1-yl]-pyrimidine and 7.5 eq benzylamine/3.5 eq N-ethyldiisopropylamine in dioxane (48 h at 90° C.) gave after deprotection (see General method for S-deprotection, Method D) (3R,5S)-1-(2-Benzylamino-pyrimidin-4-yl)-5-(2,4,5-trifluoro-benzyloxymethyl)-pyrrolidine-3-thiol; trifluoro-acetate (1:1), MS: 461 ($MH^+$);

d) (2S,4R)-2-Chloro-4-[2-(2,4,5-trifluoro-benzyloxymethyl)-4-tritylsulfanyl-pyrrolidin-1-yl]-pyrimidine and 7.5 eq butylamine/3.5 eq N-ethyldiisopropylamine in dioxane (48 h at 90° C.) gave after deprotection (see General method for S-deprotection, Method D) (3R,5S)-1-(2-Butylamino-pyrimidin-4-yl)-5-(2,4,5-trifluoro-benzyloxymethyl)-pyrrolidine-3-thiol; trifluoro-acetate (1:1), MS: 427 ($MH^+$);

e) (2S,4R)-2-Chloro-4-[2-(2,4,5-trifluoro-benzyloxymethyl)-4-tritylsulfanyl-pyrrolidin-1-yl]-pyrimidine and 30 eq methylamine solution (8.03 M in EtOH)/3.5 eq N-ethyldiisopropylamine in dioxane (48 h at 90° C.) gave after deprotection (see General method for S-deprotection, Method D) (3R,5S)-1-(2-Methylamino-pyrimidin-4-yl)-5-(2,4,5-trifluoro-benzyloxymethyl)-pyrrolidine-3-thiol; trifluoro-acetate (1:1), MS: 385 ($MH^+$).

Example 4

Suzuki-type Reactions

In general the reactions were carried out according to Stanforth, Stephen P. Catalytic cross-coupling reactions in biaryl synthesis. Tetrahedron (1998), 54(3/4), 263–303.

4.1 Method A (The Solvents Were Degased for 10 Min with Argon).

A solution of 1.35 g (2 mmol) (2S,4R)-5-Bromo-2-[2-(2,4,5-trifluoro-benzyloxymethyl)-4-tritylsulfanyl-pyrrolidin-1-yl]-pyrimidine in 12 ml dimethoxyethane were added to a suspension of 0.116 g (0.1 mmol) tetrakis (triphenylphosphine)palladium in 1.4 ml dimethoxyethane and stirred for 15 min. 0.29 g (2.4 mmol) Phenylboronic acid in 3.4 ml EtOH was then added and after 10 min, 8.8 ml of a aqueous 2 M $Na_2CO_3$ solution. The reaction was heated for 2 h at 90° C., evaporated and extracted wit $H_2O/Et_2O$ (3×). The organic phases were washed with aqueous 10% NaCl, dried ($Na_2SO_4$) and evaporated. Purification by flash-chromatography on silica gel (toluene) gave 0.48 g (36%) (2S,4R)-5-Phenyl-2-[2-(2,4,5-trifluoro-benzyloxymethyl)-4-tritylsulfanyl-pyrrolidin-1-yl]-pyrimidine, MS: 674 ($MH^+$).

TFA/triisopropylsilane deprotection (see General method for S-deprotection, Method D) gave (3R,5S)-1-(5-Phenyl-pyrimidin-2-yl)-5-(2,4,5-trifluoro-benzyloxymethyl)-pyrrolidine-3-thiol, MS: 432 ($MH^+$).

4.2 Method B (The Solvents Were Degassed for 10 Min with Argon); Parallel Synthesis:

A solution of 0.13 mmol (2S,4R)-5-Bromo-2-[2-(2,4,5-trifluoro-benzyloxymethyl)-4-tritylsulfanyl-pyrrolidin-1-yl]-pyrimidine, 0.195 mmol boronic acid or boronic acid ester and 0.004 mmol $PdCl_2$(dppf) in 2 ml dioxane and 0.4 ml 2 M $Na_2CO_3$ were heated for 48 h at 80° C. After filtration the mixture was purified by preparative HPLC (RP18, 50% to 95% Acetonitrile).

TFA/triisopropylsilane deprotection (see General method for S-deprotection, Method D) gave the free thiol.

4.3 Method C: (The Solvents Were Degased for 10 Min with Argon) [Giroux, Andre; Han, Yongxin; Prasit, Petpiboon. One pot biaryl synthesis via in situ boronate formation. Tetrahedron Lett. (1997), 38(22), 3841–3844]:

A solution of 0.68 g (1 mmol) (2S,4R)-5-Bromo-2-[2-(2,4,5-trifluoro-benzyloxymethyl)-4-tritylsulfanyl-pyrrolidin- 1-yl]-pyrimidine, 0.28 g (1.1 mmol) bis(pinacolato)diboron, 0.29 g (3 mmol, dried 2 h at 100° C., 0.1 Torr) potassium acetate and 0.024 g (0.03 mmol) PdCl$_2$(dppf) in 12 ml DMF were stirred for 4.5 h at 80° C. The reaction was cooled, treated with 0.195 ml (2 mmol) 2-bromopyridine, 0.024 g (0.03 mmol) PdCl$_2$(dppf) and 2.5 ml aqueous 2 M Na$_2$CO$_3$ solution and heated for 16 h at 80° C. The reaction evaporated (60° C./0.1 torr) and partitioned between water/Et$_2$O (3×). The organic phases were washed with aqueous 10% NaCl and dried over Na$_2$SO$_4$. Purification by flash-chromatography on silica gel (toluene/EtOAc 97.5:2.5) gave 0.125 g (2S,4R)-5-Pyridin-2-yl-2-[2-(2,4,5-trifluoro-benzyloxymethyl)-4-tritylsulfanyl-pyrrolidin-1-yl]-pyrimidine, MS: 675 (MH$^+$). TFA/triisopropylsilane deprotection (see General method for S-deprotection, Method D) gave (3R,5S)-1-(5-Pyridin-2-yl-pyrimidin-2-yl)-5-(2,4,5-trifluoro-benzyloxymethyl)-pyrrolidine-3-thiol; compound with trifluoro-acetic acid, MS: 433 (MH$^+$).

4.4 Method D: (The Solvents Were Degased for 10 Min with Argon):

A solution of 0.68 g (1 mmol) (2S,4R)-5-Bromo-2-[2-(2,4,5-trifluoro-benzyloxymethyl)-4-tritylsulfanyl-pyrrolidin-1-yl]-pyrimidine, 15 mg (0.022 mmol) of bis(triphenylphosphine)palladium(II)dichloride and 9.5 mg copper(I)iodide in 0.4 ml DMF was treated at 80° C. for 1 h with a solution of 0.35 ml (2.5 mmol) ethinyltrimethylsilane and 1.87 ml Et$_3$N in 1.5 ml DMF. The same solution was added again during 1 h and after 4 h extracted with pentane (3×)/H$_2$O (2×). The organic phase was dried (Na$_2$SO$_4$), evaporated and purified by flash-chromatography on silica gel (toluene) to give 0.063 g (9%) (2S,4R)-2-[2-(2,4,5-Trifluoro-benzyloxymethyl)-4-tritylsulfanyl-pyrrolidin-1-yl]-5-trimethylsilanylethynyl-pyrimidine, MS: 694 (MH$^+$). TFA/triisopropylsilane deprotection (see General method for S-deprotection, Method D) gave (3R,5S)-5-(2,4,5-Trifluoro-benzyloxymethyl)-1-(5-trimethylsilanylethynyl-pyrimidin-2-yl)-pyrrolidine-3-thiol, MS: 452 (MH$^+$).

According to an analogous method the following compounds were prepared via reaction of (2S,4R)-5-Bromo-2-[2-(2,4,5-trifluoro-benzyloxymethyl)-4-tritylsulfanyl-pyrrolidin-1-yl]-pyrimidine with the 2.educt mentioned in the following table 2.

Example 5

S-Acetyl-Derivatization

A solution of 397 mg (1 mmol) (3R,5S)-1-(5-Propyl-pyrimidin-2-yl)-5-(2,4,5-trifluoro-benzyloxymethyl)-pyrrolidine-3-thiol (the trifluoro-acetate salt was extracted with aqueous saturated NaHCO$_3$/EtOAc) in 6 ml pyridine were treated at 0° C. with 0.14 ml (2 mmol) acetyl chloride and stirred for 5 h at RT. The reaction was poured on ice water and extracted wit Et$_2$O (3×). The organic phases were washed with aqueous 1 N HCl and 10% NaCl, dried (Na$_2$SO$_4$) and evaporated. Flash chromatography on silica gel (CH$_2$Cl$_2$/Et$_2$O 100:0 to 95:5) gave 383 mg (87%) (3R,5S)-Thioacetic acid S-[1-(5-propyl-pyrimidin-2-yl)-5-(2,4,5-trifluoro-benzyloxymethyl)-pyrrolidin-3-yl]ester, MS: 440 (MH$^+$).

Example 6

Amines a) To 25.0 g (52.56 mmol) (2S,4R)-2-Hydroxymethyl-4-tritylsulfanyl-pyrrolidine-1-carboxylic acid tert-butyl ester in 80 ml CH$_2$Cl$_2$ were added 40 ml TFA at 0° C., and the solution was stirred at RT over night. The solution was concentrated in vacuo, and the residue was redissolved in EtOAc, washed with sat. NaHCO$_3$ solution, brine, and was dried over Na$_2$SO$_4$. 21.98 g (quant.) (2S,4R)-(4-Tritylsulfanyl-pyrrolidin-2-yl)-methanol were isolated as light brown foam.

b) The crude product was suspended in 16.46 g (105.1 mmol, 2 eq) 2-chloro-5-n-propylpyrimidine and 30 ml (175 mmol, 3.3 eq)) N-ethyl diisopropylamine and the mixture was heated to 80° C. When everything was dissolved, 350 mg (1.84 mmol) copper iodide were added, and the reaction mixture was kept at 80° C. over night. After cooling to RT, the mixture was diluted with EtOAc/H$_2$O, and the aqueous solution was extracted with EtOAc. The combined organic layers were washed with 1M KHSO$_4$, 1M HCl, and brine, and were dried with Na$_2$SO$_4$. Purification with flash chromatography with EtOAc:hexane (1:4 to 1:1) yielded 19.1 g (74%) (2S,4R)-[1-(5-Propyl-pyrimidin-2-yl)-4--tritylsulfanyl-pyrrolidin-2-yl]-methanol as light yellow foam, MS: 496 (MH$^+$).

TABLE 2

By the reaction of (2S,4R)-5-Bromo-2-(2-(2,4,5-trifluoro-benzyloxymethyl)-4-tritylsulfanyl-pyrrolidin-1-yl)-pyrimidine 68-5011 with the 2.educt following method B.

| NAME | 2. Educt | MS | | COLOR |
|---|---|---|---|---|
| (3R,5S)-1-(5-Pyridin-4-yl-pyrimidin-2-yl)-5-(2,4,5-trifluoro-benzyloxymethyl)-pyrrolidine-3-thiol | 4-PYRIDYLBORONIC ACID | 433 | M+H+ | orange |
| (3R,5S)-1-(5-Thiophen-3-yl-pyrimidin-2-yl)-5-(2,4,5-trifluoro-benzyloxymethyl)-pyrrolidine-3-thiol | THIOPHENE-3-BORONIC ACID | 438 | M+H+ | |
| (3R,5S)-1-[5-(4-Methoxy-phenyl)-pyrimidin-2-yl]-5-(2,4,5-trifluoro-benzyloxy methyl)-pyrrolidine-3-thiol | 4-METHOXY-BENZENEBORONIC ACID | 462 | M+H+ | |
| (2S,4R)-4-{2-[4-Mercapto-2-(2,4,5-trifluoro-benzyloxy methyl)-pyrrolidin-1-yl]-pyrimidin-5-yl}-benzoic acid | 4-CARBOXY-BENZENEBORONIC ACID | 476 | M+H+ | |
| (3R,5S)-1-(5-Allyl-pyrimidin-2-yl)-5-(2,4,5-trifluoro-benzyloxy methyl)-pyrrolidine-3-thiol | 2-ALLYL-4,4,5,5-TETRAMETHYL-1,3,2-DIOXA-BOROLAN | 396 | M+H+ | |
| (3R,5S)-1-(5-Pyridin-3-yl-pyrimidin-2-yl)-5-(2,4,5-trifluoro-benzyloxymethyl)-pyrrolidine-3-thiol | PYRIDINE-3-BORONIC ACID 1,3-PROPANEDIOL | 433 | M+H+ | | c) 1.0 g (2.0 mmol) (2S,4R)-[1-(5-Propyl-pyrimidin-2-yl)-4-tritylsulfanyl-pyrrolidin-2-yl]-methanol in 15 ml THF were treated with 764 mg (2.82 mmol) triphenyl phosphine and 420 mg (2.82 mmol) phthalimide at RT. The solution was cooled to 0° C. and 615 µl (3.83 mmol) diethylazo dicarboxylate in 3 ml THF were added. The solution was stirred at RT over night, H$_2$O was added and the inorganic layer was extracted with ETOAc. The combined layers were washed with 1M NaOH, sat. NaHCO$_3$ solution and brine, and were dried over Na$_2$SO$_4$. Column chromatography with EtOAc:hexane 1:2 as eluent yielded 1.20 g (95%) (2S,4R)-2-[1-(5-Propyl-pyrimidin-2-yl)-4-tritylsulfanyl-pyrrolidin-2-ylmethyl]-isoindole-1,3-dione as white solid, MS: 625 (MH$^+$).

d) 960 mg (1.52 mmol) (2S,4R)-2-[1-(5-Propyl-pyrimidin-2-yl)-4-tritylsulfanyl-pyrrolidin-2-ylmethyl]-isoindole-1,3-dione in 95 ml ethanol were treated with 2.4 ml (49.4 mmol) hydrazine hydrate at reflux. After cooling to RT, the solution was filtered and concentrated, the crude product was purified by flash chromatography with CH$_2$Cl$_2$:MeOH:NH$_4$OH 90:10:0.25 yielding 659 mg (88%) (2S,4R)-C-[1-(5-Propyl-pyrimidin-2-yl)-4-tritylsulfanyl-pyrrolidin-2-yl]-methylamine as white foam, MS: 495 (MH$^+$).

e) To 643 mg (1.3 mmol) (2S,4R)-C-[1-(5-Propyl-pyrimidin-2-yl)-4-tritylsulfanyl-pyrrolidin-2-yl]-methylamine in 3 ml methanol were added 158 µl (1.43 mmol) 2,5-difluorobenzaldehyde and 5 ml methanol to partially redissolve the compound. This was followed by a solution of 108 mg (0.78 mmol) zinc chloride and 109 mg (1.56 mmol) NaBH$_3$CN in 3 ml methanol. The solution was stirred over night, concentrated and dissolved in ETOAc/sat NaHCO$_3$ solution. The inorganic layer was extracted with EtOAc, the combined organic layers were washed with NaHCO$_3$ and brine, dried over Na$_2$SO$_4$ and evaporated. Purification with column chromatography yielded 750 mg (93%) (2S,4R)-(2,5-Difluoro-benzyl)-[1-(5-propyl-pyrimidin-2-yl)-4-tritylsulfanyl-pyrrolidin-2-ylmethyl]-amine as light yellow gum, MS: 621 (MH$^+$).

f) 160 mg (0.258 mmol) (2S,4R)-(2,5-Difluoro-benzyl)-[1-(5-propyl-pyrimidin-2-yl)-4-tritylsulfanyl-pyrrolidin-2-ylmethyl]-amine in 2 ml pyridine were treated with 37 µl (0.52 mmol) acetyl chloride at 0° C. The solution was stirred at RT for 1.5 h, poured on ice water and was extracted with EtOAc. The combined organic layers were washed with 1N HCl and brine, dried over Na$_2$SO$_4$ and were evaporated. Column chromatography with EtOAc:hexane 1:2 to 1:1 yielded 170 mg (quant) (2S,4R)-N-(2,5-Difluoro-benzyl)-N-[1-(5-propyl-pyrimidin-2-yl)-4-tritylsulfanyl-pyrrolidin-2-ylmethyl]-acetamide as white foam.

g) From (2S,4R)-N-(2,5-Difluoro-benzyl)-N-[1-(5-propyl-pyrimidin-2-yl)-4-tritylsulfanyl-pyrrolidin-2-ylmethyl]-acetamide was prepared analogously to general procedure E (2S,4R)-N-(2,5-Difluoro-benzyl)-N-[4-mercapto-1-(5-propyl-pyrimidin-2-yl)-pyrrolidin-2-ylmethyl]-acetamide as colorless gum, MS: 421 (MH$^+$).

h) From (2S,4R)-(2,5-Difluoro-benzyl)-[1-(5-propyl-pyrimidin-2-yl)-4-tritylsulfanyl-pyrrolidin-2-ylmethyl]-amine was prepared analogously to general procedure E (2S,4R)-5-[(2,5-Difluoro-benzylamino)-methyl]-1-(5-propyl-pyrimidin-2-yl)-pyrrolidine-3-thiol as colorless gum, MS: 379 (MH$^+$).

i) 50 mg (0.13 mmol) (2S,4R)-5-[(2,5-Difluoro-benzylamino)-methyl]-1-(5-propyl-pyrimidin-2-yl)-pyrrolidine-3-thiol in 1 ml pyridine were treated with 28 µl (0.39 mmol) acetyl chloride at 0° C. The solution was stirred at RT for 1.5 h, poured on ice water and was extracted with EtOAc. The combined organic layers were washed with 1N HCl and brine, dried over Na$_2$SO$_4$ and were evaporated. Column chromatography with EtOAc:hexane 1:1 to 2:1 yielded 54 mg (88%) (3R,5S)-Thioacetic acid S-[5-[[acetyl-(2,5-difluoro-benzyl)-amino]-methyl]-1-(5-propyl-pyrimidin-2-yl)-pyrrolidin-3-yl]ester as off-white gum, Ms: 463 (MH$^+$).

j) 220 mg (0.35 mmol) (2S,4R)-(2,5-Difluoro-benzyl)-[1-(5-propyl-pyrimidin-2-yl)-4-tritylsulfanyl-pyrrolidin-2-ylmethyl]-amine in 6.5 ml CH$_2$Cl$_2$ were treated with 74 µl (0.43 mmol) N-ethyl diisopropylamine, 63 µl (0.43 mmol) chloro benzyl formate and 26.6 mg (0.043 mmol) DMAP polymer bound at 0° C. for 5 min, and 1 h at RT. 212 mg (0.212 mmol) polymer bound trisamine were added and the solution was shaken over night. Filtration and concentration yielded 331 mg (quant) (2S,4R)-(2,5-Difluoro-benzyl)-[1-(5-propyl-pyrimidin-2-yl)-4-tritylsulfanyl-pyrrolidin-2-ylmethyl]-carbamic acid benzyl ester as white foam, which were treated according to procedure E to give: (2S,4R)-(2,5-Difluoro-benzyl)-[4-mercapto-1-(5-propyl-pyrimidin-2-yl)-pyrrolidin-2-ylmethyl]-carbamic acid benzyl ester as colorless foam, MS: 513 (MH$^+$).

k) From (2S,4R)-(2,5-Difluoro-benzyl)-[4-mercapto-1-(5-propyl-pyrimidin-2-yl)-pyrrolidin-2-ylmethyl]-carbamic acid benzyl ester was prepared analogously to example 6 g (3R,5S)-Thioacetic acid S-[5-[[benzyloxycarbonyl-(2,5-difluoro-benzyl)-amino]-methyl]-1-(5-propyl-pyrimidin-2-yl)-pyrrolidin-3-yl]ester.

l) To 137 mg (2.5 mmol) (3R,5S)-Thioacetic acid S-[5-[[benzyloxycarbonyl-(2,5-difluoro-benzyl)-amino]-methyl]-1-(5-propyl-pyrimidin-2-yl)-pyrrolidin-3-yl]ester in 5 ml EE were added 320 µl 33% HBr in acetic acid at 0° C. The solution was stirred at RT for 12 h, poured on NaHCO$_3$ and the inorganic phase was extracted with EtOAc. The combined organic layers were washed with brine, dried over Na$_2$SO$_4$ and were evaporated. Purification with column chromatography with EtOAc as eluent yielded 65 mg (63%) (3R,5S)-Thioacetic acid S-[5-[(2,5-difluoro-benzylamino)-methyl]-1-(5-propyl-pyrimidin-2-yl)-pyrrolidin-3-yl]ester as colorless oil, MS: 421(MH$^+$). (Nicht in Liste).

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| | |
|---|---|
| Compound of formula I | 3.0 mg |
| Gelatine | 150.0 mg |
| Phenol | 4.7 mg |
| Water for injection solutions | ad 1.0 ml |

Example D 500 mg of compound of formula I are suspended in 3.5 ml of Myglyol 812 and 0.08 g of benzyl alcohol. This suspension is filled into a container having a dosage valve. 5.0 g of Freon 12 under pressure are filled into the container through the valve. The Freon is dissolved in the Myglyol-benzyl alcohol mixture by shaking. This spray container contains about 100 single dosages which can be applied individually.

What is claimed is:

1. A compound selected from the group consisting of compounds of formula I

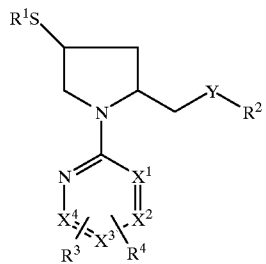

(I)

wherein $R^1$ is hydrogen, alkylcarbonyl or arylcarbonyl;

$R^2$ is alkyl, alkinyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl(alkoxycarbonyl)alkyl, arylaminocarbonyl, diarylalkyl, aryl(carboxyalkyl)aminocarbonyl, arylcarbonyl, arylsulfonyl, cycloalkyl, cycloalkylcarbonyl, cycloalkylalkyl, heteroaryl, heteroarylalkyl, heterocyclylalkyl or the group $YR^2$ is heterocyclyl;

$R^3$ and $R^4$ are independently selected from the group consisting of hydrogen, alkyl, alkylcycloalkyl, alkylcycloalkylalkyl, alkylthio, cycloalkyl, cycloalkylalkyl, carbamoyl, carboxy, carboxyalkyl, cyano, amino, mono- and dialkylamino, alkoxy, alkoxyalkyl, alkoxycarbonyl, alkoxycarbonylalkyl, alkenyl, alkinyl, aryl, arylalkyl, arylalkyl(alkoxycarbonyl)alkyl, arylcarbonylalkyl, arylalkenyl, aryl(alkoxycarbonyl)alkyl, arylamino, arylalkylamino, aryloxy, halogen, heteroaryl, heteroarylalkyl, heterocyclyl, heterocyclylalkyl, trimethylsilanylethynyl or trifluormethyl;

$R^5$ is hydrogen, alkyl, aryl, arylalkyloxycarbonyl, or alkylcarbonyl;

$X^1$, $X^2$, $X^3$ and $X^4$ are CH or N with the proviso that only up to two of $X^1$, $X^2$, $X^3$ and $X^4$ are N; and Y is —O— or —$NR^5$—;

pharmaceutically acceptable esters and pharmaceutically acceptable salts thereof.

2. The compound according to claim 1 of formula II

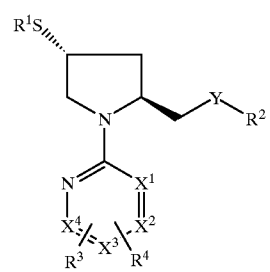

(II)

wherein $R^1$, $R^2$, $R^3$, $R^4$, $X^1$, $X^2$, $X^3$, $X^4$ and Y are as defined in formula 1.

3. The compound according to claim 1 wherein $R^1$ is hydrogen or alkylcarbonyl.

4. The compound according to claim 3 wherein said alkylcarbonyl is acetyl.

5. The compound according to claim 1 wherein $R^1$ is hydrogen.

6. The compound according to claim 1 wherein $R^2$ is alkyl, alkinyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl(alkoxycarbonyl)alkyl, diarylalkyl, aryl(carboxyalkyl)aminocarbonyl, arylcarbonyl, arylsulfonyl, cycloalkyl, cycloalkylcarbonyl, cycloalkylalkyl, heteroaryl, heteroarylalkyl, heterocyclylalkyl or arylaminocarbonyl which is arylcarbamoyl.

7. The compound according to claim 1 wherein $R^2$ is aryl, arylalkyl, arylalkoxyalkyl, arylaminocarbonyl, arylcarbonyl, arylsulfonyl, cycloalkyl, cycloalkylcarbonyl, cycloalkylalkyl or heteroarylalkyl.

8. The compound according to claim 1 wherein $R^2$ is aryl, arylalkyl, arylcarbonyl, arylsulfonyl, heteroarylalkyl, or arylaminocarbonyl which is arylcarbamoyl.

9. The compound according to claim 8 wherein $R^2$ is arylalkyl.

10. The compound according to claim 9 wherein arylalkyl of $R^2$ is phenylalkyl or phenylalkyl substituted with 2 or 3 halogen atoms.

11. The compound according to claim 1 wherein $R^3$ and $R^4$ are independently selected from the group consisting of hydrogen, alkyl, alkylthio, alkenyl, alkoxy, alkoxycarbonyl, amino, aryl, arylalkyl, arylalkenyl, arylalkylamino, aryloxy, mono- and dialkylamino, carbamoyl, carboxy, cyano, halogen, heteroaryl, heteroarylalkyl, trimethylsilanylethynyl and trifluoromethyl.

12. The compound according to claim 1 wherein $R^3$ and $R^4$ are independently selected from the group consisting of hydrogen, alkyl, alkoxy, alkoxycarbonyl, alkenyl, thiophenyl, amino, mono- and dialkylamino, carboxy, cyano, halogen, trimethylsilanylethynyl, phenylalkylamino, pyridinylpyrimidinyl, pyrazinyl, phenyl, and phenoxy, wherein the aryl and heteroaryl groups of said thiophenyl, phenylalkylamino, pyridinyl, pyrimidinyl, pyrazinyl, phenyl and phenoxy are optionally substituted with alkyl, alkoxy, carboxy, or halogen.

13. The compound according to claim 12 wherein $R^3$ is hydrogen, alkyl, alkoxy, alkoxycarbonyl, alkenyl, thiophenyl, amino, mono- and dialkylamino, carboxy, cyano, halogen, trimethylsilanylethynyl, phenylalkylamino, pyridinyl, pyrimidinyl, pyrazinyl, phenyl, and phenoxy, wherein the aryl and heteroaryl groups of said thiophenyl, phenylalkylamino, pyridinyl, pyrimidinyl, pyrazinyl, phenyl and phenoxy are optionally substituted with alkyl, alkoxy, carboxy or halogen, and wherein $R^4$ is hydrogen.

14. The compound according to claim 1 wherein Y is —$NR^5$—.

15. The compound according to claim 1 wherein $R^5$ is alkyl.

16. The compound according to claim 1 wherein $R^5$ is hydrogen.

17. The compound according to claim 1 wherein Y is —O—.

18. The compound according to claim 1 wherein $X^1$ is N and $X^2$, $X^3$ and $X^4$ are each CH.

19. The compound according to claim 1 wherein $X^2$ is N and $X^1$, $X^3$ and $X^4$ are each CH.

20. The compound according to claim 1 wherein $X^3$ is N and $X^1$, $X^2$ and $X^4$ are each CH.

21. The compound according to claim 1 wherein $X^1$, $X^2$, $X^3$ and $X^4$ are each CH.

22. The compound according to claim 1 wherein
 $R^1$ is hydrogen or alkylcarbonyl;
 $R^2$ is arylalkyl which is phenylalkyl substituted with 2 or 3 halogen atoms;
 $R^3$ is hydrogen, alkyl, alkoxy, alkoxycarbonyl, alkenyl, thiophenyl, amino, mono- and dialkylamino, carboxy, cyano, halogen, trimethylsilanylethynyl, phenylalkylamino, pyridinyl, pyrimidinyl, pyrazinyl, phenyl, or phenoxy, and wherein the aryl and heteroaryl groups of said thiophenyl, phenylalkylamino, pyridinyl, pyrimidinyl, pyrazinyl, phenyl and phenoxy are optionally substituted with alkyl, alkoxy, carboxy, or halogen;
 $R^4$ is hydrogen;
 $X^1$, $X^2$, $X^3$ and $X^4$ are CH or N with the proviso that only up to two groups of $X^1$, $X^2$, $X^3$ and $X^4$ are N; and
 Y is —NH— or —O—.

23. The compound according to claim 22 wherein said alkylcarbonyl of $R^1$ is acetyl, and $R^2$ is difluorobenzyl or trifluorobenzyl.

24. The compound according to claim 1 selected from the group consisting of:
 a) (3R,5S)-1-pyrimidin-2-yl-5-(2,4,5-trifluoro-benzyloxymethyl)-pyrrolidine-3-thiol trifluoro-acetate (1:1);
 b) (3R,5S)-1-(4,6-dimethoxy-pyrimidin-2-yl)-5-(2,4,5-trifluoro-benzyloxymethyl)-pyrrolidine-3-thiol;
 c) (3R,5S)-1-(4-amino-5-fluoro-pyrimidin-2-yl)-5-(2,4,5-trifluoro-benzyloxymethyl)-pyrrolidin-3-thiol;
 d) 2-[(2S,4R)-4-mercapto-2-(2,4,5-trifluoro-benzyloxymethyl)-pyrrolidin-1-yl]-nicotinonitrile;
 e) (3R,5S)-1-(6-phenyl-pyridazin-3-yl)-5-(2,4,5-trifluoro-benzyloxymethyl)-pyrrolidine-3-thiol;
 f) 2-[(2S,4R)-4-mercapto-2-(2,4,5-trifluoro-benzyloxymethyl)-pyrrolidin-1-yl]-nicotinic acid;
 g) 2-[(2S,4R)-4-mercapto-2-(2,4,5-trifluoro-benzyloxymethyl)-pyrrolidin-1-yl]-6-methyl-pyrimidine-4-carboxylic acid methyl ester;
 h) 2-[(2S,4R)-4-mercapto-2-(2,4,5-trifluoro-benzyloxymethyl)-pyrrolidin-1-yl]-4-trifluoromethyl-pyrimidine-5-carboxylic acid methyl ester;
 i) (3R,5S)-1-pyrazin-2-yl-5-(2,4,5-trifluoro-benzyloxymethyl)-pyrrolidine-3-thiol trifluoro-acetate;
 j) 2-[(2S,4R)-4-mercapto-2-(2,4,5-trifluoro-benzyloxymethyl)-pyrrolidin-1-yl]-nicotinamide;
 k) (3R,5S)-5-(2,5-difluoro-4-methoxy-benzyloxymethyl)-1-(2-methoxy-pyrimidin-4-yl)-pyrrolidine-3-thiol;
 l) (3R,5S)-1-(2-chloro-pyrimidin-4-yl)-5-(2,4,5-trifluoro-benzyloxymethyl)-pyrrolidine-3-thiol trifluoro-acetate;
 m) (3R,5S)-1-(5-ethyl-pyrimidin-2-yl)-5-(2,4,5-trifluoro-benzyloxymethyl)-pyrrolidine-3-thiol trifluoro-acetate (1:1);
 n) (3R,5S)-1-(5-propyl-pyrimidin-2-yl)-5-(2,4,5-trifluoro-benzyloxymethyl)-pyrrolidine-3-thiol trifluoro-acetate (1:1);
 o) (3R,5S)-5-(2,4,5-trifluoro-benzyloxymethyl)-1-(4-trifluoromethyl-pyrimidin-2-yl)-pyrrolidine-3-thiol trifluoro-acetate (1:1);
 p) (3R,5S)-5-(2,4,5-trifluoro-benzyloxymethyl)-1-(5-trifluoromethyl-pyridin-2-yl)-pyrrolidine-3-thiol trifluoro-acetate (1:1);
 q) (3R,5S)-1-pyridin-2-yl-5-(2,4,5-trifluoro-benzyloxymethyl)-pyrrolidine-3-thiol trifluoro-acetate (1:1);
 r) (2S,4R)-2-[4-mercapto-2-(2,4,5-trifluoro-benzyloxymethyl)-pyrrolidin-1-yl]-6-methyl-pyrimidine-4-carboxylic acid;
 s) (3R,5S)-1-(2-methoxy-pyrimidin-4-yl)-5-(2,4,5-trifluoro-benzyloxymethyl)-pyrrolidine-3-thiol;
 t) (3R,5S)-1-(2-phenylamino-pyrimidin-4-yl)-5-(2,4,5-trifluoro-benzyloxymethyl)-pyrrolidine-3-thiol trifluoro-acetate (1:1);
 u) (3R,5S)-1-(2-benzylamino-pyrimidin-4-yl)-5-(2,4,5-trifluoro-benzyloxymethyl)-pyrrolidine-3-thiol; trifluoro-acetate (1:1);
 v) (3R,5S)-1-(2-methylamino-pyrimidin-4-yl)-5-(2,4,5-trifluoro-benzyloxymethyl)-pyrrolidine-3-thiol; trifluoro-acetate (1:1);
 w) (3R,5S) 1-(2-butylamino-pyrimidin-4-yl)-5-(2,4,5-trifluoro-benzyloxymethyl)-pyrrolidine-3-thiol; trifluoro-acetate (1:1);
 x) (3R,5S)-1-(2-methylsulfanyl-pyrimidin-4-yl)-5-(2,4,5-trifluoro-benzyloxymethyl)-pyrrolidine-3-thiol;
 y) (3R,5S)-1-(2-phenoxy-pyrimidin-4-yl)-5-(2,4,5-trifluoro-benzyloxymethyl)-pyrrolidine-3-thiol;
 z) (3R,5S)-1-(5-phenyl-pyrimidin-2-yl)-5-(2,4,5-trifluoro-benzyloxymethyl)-pyrrolidine-3-thiol;
 aa) (3R,5S)-1-(5-pyridin-2-yl-pyrimidin-2-yl)-5-(2,4,5-trifluoro-benzyloxymethyl)-pyrrolidine-3-thiol; compound with trifluoro-acetic acid;
 bb) (3R,5S)-1-(5-pyridin-4-yl-pyrimidin-2-yl)-5-(2,4,5-trifluoro-benzyloxymethyl)-pyrrolidine-3-thiol;
 cc) (3R,5S)-1-(5-thiophen-3-yl-pyrimidin-2-yl)-5-(2,4,5-trifluoro-benzyloxymethyl)-pyrrolidine-3-thiol;
 dd) (3R,5S)-1-[5-(4-methoxy-phenyl)-pyrimidin-2-yl]-5-(2,4,5-trifluoro-benzyloxymethyl)-pyrrolidine-3-thiol;
 ee) (2S,4R)-4-{2-[4-mercapto-2-(2,4,5-trifluoro-benzyloxymethyl)-pyrrolidin-1-yl]-pyrimidin-5-yl}-benzoic acid;
 ff) (3R,5S)-1-(5-allyl-pyrimidin-2-yl)-5-(2,4,5-trifluoro-benzyloxymethyl)-pyrrolidine-3-thiol;
 gg) (3R,5S)-1-(5-pyridin-3-yl-pyrimidin-2-yl)-5-(2,4,5-trifluoro-benzyloxymethyl)-pyrrolidine-3-thiol; and
 hh) (3R,5S)-5-(2,4,5-trifluoro-benzyloxymethyl)-1-(5-trimethylsilanylethynyl-pyrimidin-2-yl)-pyrrolidine-3-thiol.

25. The compound according to claim 1 selected from the group consisting of:
 a) (3R,5S)-1-pyrimidin-2-yl-5-(2,4,5-trifluoro-benzyloxymethyl)-pyrrolidine-3-thiol trifluoro-acetate (1:1);

b) (3R,5S)-1-(6-phenyl-pyridazin-3-yl)-5-(2,4,5-trifluoro-benzyloxymethyl)-pyrrolidine-3-thiol;

c) (3R,5S)-1-pyrazin-2-yl-5-(2,4,5-trifluoro-benzyloxymethyl)-pyrrolidine-3-thiol; compound with trifluoro-acetic acid;

d) (3R,5S)-1-(5-ethyl-pyrimidin-2-yl)-5-(2,4,5-trifluoro-benzyloxymethyl)-pyrrolidine-3-thiol trifluoro-acetate (1:1);

e) (3R,5S)-1-(5-propyl-pyrimidin-2-yl)-5-(2,4,5-trifluoro-benzyloxymethyl)-pyrrolidine-3-thiol trifluoro-acetate (1:1);

f) (3R,5S)-5-(2,4,5-trifluoro-benzyloxymethyl)-1-(5-trifluoromethyl-pyridin-2-yl)-pyrrolidine-3-thiol trifluoro-acetate (1:1);

g) (3R,5S)-1-(5-phenyl-pyrimidin-2-yl)-5-(2,4,5-trifluoro-benzyloxymethyl)-pyrrolidine-3-thiol;

h) (3R,5S)-thioacetic acid S-[1-(5-propyl-pyrimidin-2-yl)-5-(2,4,5-trifluoro-benzyloxymethyl)-pyrrodin-3-yl] ester;

i) (3R,5S)-1-(5-pyridin-2-yl-pyrimidin-2-yl)-5-(2,4,5-trifluoro-benzyloxymethyl)-pyrrolidine-3-thiol trifluoro-acetate;

j) (3R,5S)-1-(5-pyridin-4-yl-pyrimidin-2-yl)-5-(2,4,5-trifluoro-benzyloxymethyl)-pyrrolidine-3-thiol;

k) 1-(5-thiophen-3-yl-pyrimidin-2-yl)-5-(2,4,5-trifluoro-benzyloxymethyl)-pyrrolidine-3-thiol;

l) 1-(5-pyridin-3-yl-pyrimidin-2-yl)-5-(2,4,5-trifluoro-benzyloxymethyl)-pyrrolidine-3-thiol;

m) (2S,4R)-5-[(2,5-difluoro-benzylamino)-methyl]-1-(5-propyl-pyrimidin-2-yl)-pyrrolidine-3-thiol; and n) (3R,5S)-thioacetic acid S-[5-[(2,5-difluoro-benzylamino)-methyl]-1-(5-propyl-pyrimidin-2-yl)-pyrrolidin-3-yl]ester.

26. A pharmaceutical composition comprising a compound according to claim 1 and a pharmaceutically acceptable excipient.

27. A dimeric form of a compound of formula I

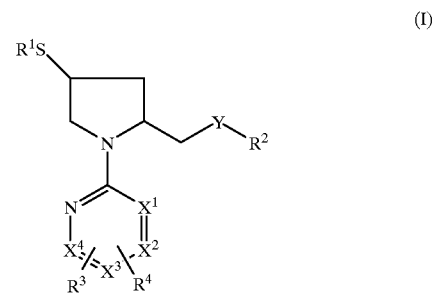

(I)

wherein
$R^1$ is hydrogen, alkylcarbonyl or arylcarbonyl;
$R^2$ is alkyl, alkinyl, hydroxyalkyl, carboxyalkyl, alkoxycarbonyl, alkylcarbonylalkyl, alkylcycloalkyl, alkylcycloalkylalkyl, alkylsulfonyl, aryl, arylalkyl, arylalkoxyalkyl, aryl(alkoxycarbonyl)alkyl, arylaminocarbonyl, diarylalkyl, aryl(carboxyalkyl)aminocarbonyl, arylcarbonyl, arylsulfonyl, cycloalkyl, cycloalkylcarbonyl, cycloalkylalkyl, heteroaryl, heteroarylalkyl, heterocyclylalkyl or the group $YR^2$ is heterocyclyl;
$R^3$ and $R^4$ are independently selected from the group consisting of hydrogen, alkyl, alkylcycloalkyl, alkylcycloalkylalkyl, alkylthio, cycloalkyl, cycloalkylalkyl, carbamoyl, carboxy, carboxyalkyl, cyano, amino, mono- and dialkylamino, alkoxy, alkoxyalkyl, alkoxycarbonyl, alkoxycarbonylalkyl, alkenyl, alkinyl, aryl, arylalkyl, arylalkyl(alkoxycarbonyl)alkyl, arylcarbonylalkyl, arylalkenyl, aryl(alkoxycarbonyl)alkyl, arylamino, arylalkylamino, aryloxy, halogen, heteroaryl, heteroarylalkyl, heterocyclyl, heterocyclylalkyl, trimethylsilanylethynyl or trifluormethyl;
$R^5$ is hydrogen, alkyl, aryl, arylalkyloxycarbonyl, or alkylcarbonyl;
$X^1$, $X^2$, $X^3$ and $X^4$ are CH or N with the proviso that only up to two of $X^1$, $X^2$, $X^3$ and $X^4$ are N; and
Y is —O— or —NR$^5$—.

28. A pharmaceutical composition comprising a dimeric form of a compound according to claim 27 and a pharmaceutically acceptable excipient.

* * * * *